United States Patent
Mancebo

(10) Patent No.: US 10,501,785 B2
(45) Date of Patent: Dec. 10, 2019

(54) REAGENTS AND METHODS FOR AUTOLIGATION CHAIN REACTION

(71) Applicant: Ricardo Mancebo, Fremont, CA (US)

(72) Inventor: Ricardo Mancebo, Fremont, CA (US)

(73) Assignee: Ricardo Mancebo, Fremont, CA (US)

( * ) Notice: Subject to any disclaimer, the term of this patent is extended or adjusted under 35 U.S.C. 154(b) by 308 days.

(21) Appl. No.: 15/635,072

(22) Filed: Jun. 27, 2017

(65) Prior Publication Data

US 2017/0298428 A1    Oct. 19, 2017

Related U.S. Application Data

(62) Division of application No. 14/370,446, filed as application No. PCT/US2012/072192 on Dec. 28, 2012, now Pat. No. 97,255,761.

(60) Provisional application No. 61/580,988, filed on Dec. 28, 2011.

(51) Int. Cl.
    *C12Q 1/68* (2018.01)
    *C12Q 1/6853* (2018.01)
    *C12Q 1/6862* (2018.01)

(52) U.S. Cl.
    CPC ........ *C12Q 1/6853* (2013.01); *C12Q 1/6862* (2013.01)

(58) Field of Classification Search
    None
    See application file for complete search history.

(56) References Cited

U.S. PATENT DOCUMENTS

| | | | |
|---|---|---|---|
| 5,616,464 A * | 4/1997 | Albagli | B01L 7/52 435/6.1 |
| 6,955,901 B2 | 10/2005 | Schouten | |
| 7,387,887 B2 | 6/2008 | Wittwer et al. | |
| 7,456,281 B2 | 11/2008 | Wittwer et al. | |
| 7,582,429 B2 | 9/2009 | Wittwer et al. | |
| 9,725,761 B2 | 8/2017 | Mancebo | |
| 2005/0118616 A1* | 6/2005 | Kawashima | C12Q 1/682 435/6.12 |
| 2010/0183634 A1 | 7/2010 | Luo et al. | |
| 2010/0267585 A1 | 10/2010 | Terbrueggen | |
| 2011/0312703 A1 | 12/2011 | Facer et al. | |
| 2013/0210079 A1 | 8/2013 | Stanojevic et al. | |

FOREIGN PATENT DOCUMENTS

| | | |
|---|---|---|
| WO | WO-2010129672 A1 | 11/2010 |
| WO | WO-2013102150 A1 | 7/2013 |

OTHER PUBLICATIONS

Xu et al. (High sequence fidelity in a non-enzymatic DNA autoligation reaction, Nucl. Acids Res. (1999) 27 (3): 875-881, Feb. 1999).*
El-Sagheer et al. (Synthesis and Polymerase Chain Reaction Amplification of DNA Strands Containing an Unnatural Triazole Linkage, J Ann Chem Soc. Mar. 25, 2009;131(11):3958-64).*

(Continued)

*Primary Examiner* — Aaron A Priest
(74) *Attorney, Agent, or Firm* — Wilson, Sonsini, Goodrich & Rosati

(57) ABSTRACT

The invention relates to the amplification of specific target nucleic acids. The invention provides methods, reagents, and kits for carrying out such amplification via the autoligation chain reaction (ACR).

40 Claims, 21 Drawing Sheets

Specification includes a Sequence Listing.

| Oligo | Oligo Sequence | Modification | Position |
|---|---|---|---|
| ACR Primer 1 | GCTCCTCGTGGG/iFluorT/GAC/3AzideN/ | Azide | 3' |
| ACR Primer 2 | /5Hexynyl/G/i6-TAMN/ACGCTGGCGCCGGTC | Hexynyl Alkyne | 5' |
| Rev HEX Template | GGCAGCTCCTCGTGGGTGACGACGCTGGCGCCGGTCACCT | | |
| ACR Primer 3 | /5Hexynyl/GTCACCCACGAGGAGC | Hexynyl Alkyne | 5' |
| ACR Primer 4 | GACCGGCGCCAGCGTC/3AzideN/ | Azide | 3' |
| Fwd HEX Template | AGGTGACCGGCGCCAGCGTCGTCACCCACGAGGAGCTGCC | | |
| ACR Primer 5 | TCGTGGG/iFluorT/GACGACGC/3AzideN/ | Azide | 3' |
| ACR Primer 6 | /55OCTdU/i6-TAMN/GGCGCCGGTCACCTC | Octadiynyl Alkyne | 5' |
| Rev OCT Template | CTCCTCGTGGGTGACGACGCTGGCGCCGGTCACCTCCTCG | | |
| ACR Primer 7 | /55OCTdU/CGTCACCCACGAGGA | Octadiynyl Alkyne | 5' |
| ACR Primer 8 | GTGACCGGCGCCAGCG/3AzideN/ | Azide | 3' |
| Fwd OCT Template | CGAGGAGGTGACCGGCGCCAGCGTCGTCACCCACGAGGAG | | |

(56) References Cited

OTHER PUBLICATIONS

Abe, et al. Flow cytometric detection of specific RNAs in native human cells with quenched autoligating FRET probes. Proc Natl Acad Sci U S A. Jan. 10, 2006;103(2):263-8. Epub Dec. 29, 2005.

Abe, et al. Rapid DNA chemical ligation for amplification of RNA and DNA signal. Bioconjug Chem. Jan. 2008;19(1):327-33. Epub Nov. 9, 2007.

Al-Soud, et al. Purification and characterization of PCR-inhibitory components in blood cells. J Clin Microbiol. Feb. 2001;39(2):485-93.

Currell. Analytical Instrumentation: Performance Characteristics and Quality, John Wiley & Sons, Inc. (2000).

Didenko. DNA probes using fluorescence resonance energy transfer (FRET): designs and applications. Biotechniques. Nov. 2001;31(5):1106-16, 1118, 1120-1.

El-Sagheer, et al. Synthesis and polymerase chain reaction amplification of DNA strands containing an unnatural triazole linkage. J Am Chem Soc. Mar. 25, 2009;131(11):3958-64. doi: 10.1021/ja8065896.

European search report and search opinion dated Sep. 28, 2015 for EP Application No. 12862641.3.

Franzini, et al. 7-Azidomethoxy-coumarins as profluorophores for templated nucleic acid detection. Chembiochem. Dec. 15, 2008;9(18):2981-8. doi: 10.1002/cbic.200800507.

Franzini, et al. Efficient nucleic acid detection by templated reductive quencher release. J Am Chem Soc. Nov. 11, 2009;131(44):16021-3. doi: 10.1021/ja904138v.

Honore-Bouakline, et al. Rapid diagnosis of extrapulmonary tuberculosis by PCR: impact of sample preparation and DNA extraction. J Clin Microbiol. Jun. 2003;41(6):2323-9.

Huggett, et al. Differential susceptibility of PCR reactions to inhibitors: an important and unrecognised phenomenon. BMC Res Notes. Aug. 28, 2008;1:70. doi: 10.1186/1756-0500-1-70.

International search report and written opinion dated May 3, 2013 for PCT/US2012/072192.

Lane, et al. The thermodynamic advantage of DNA oligonucleotide 'stacking hybridization' reactions: energetics of a DNA nick. Nucleic Acids Res. Feb. 1, 1997;25(3):611-7.

Meena, et al. 2',3'-Dideoxy-3'-thionucleoside triphosphates: syntheses and polymerase substrate activities. Org Lett. Mar. 15, 2007;9(6):1161-3. Epub Feb. 24, 2007.

Miller, et al. New, stronger nucleophiles for nucleic acid-templated chemistry: Synthesis and application in fluorescence detection of cellular RNA. Bioorg Med Chem. Jan. 1, 2008;16(1):56-64. Epub May 3, 2007.

Moses, et al. The growing applications of click chemistry. Chem Soc Rev. Aug. 2007;36(8):1249-62. Epub May 3, 2007.

Ochert, et al. Inhibitory effect of salivary fluids on PCR: potency and removal. PCR Methods Appl. Jun. 1994;3(6):365-8.

Ratnamohan, et al. Removal of inhibitors of CSF-PCR to improve diagnosis of herpesviral encephalitis. J Virol Methods. May 1998;72(1):59-65.

Rostovtsev, et al. A stepwise huisgen cycloaddition process: copper(I)-catalyzed regioselective "ligation" of azides and terminal alkynes. Angew Chem Int Ed Engl. Jul. 15, 2002;41(14):2596-9.

Sabbagh, et al. Synthesis of phosphorothioamidites derived from 3'-thio-3'-deoxythymidine and 3'-thio-2',3'-dideoxycytidine and the automated synthesis of oligodeoxynucleotides containing a 3'-S-phosphorothiolate linkage. Nucleic Acids Res. Jan. 23, 2004;32(2):495-501. Print 2004.

Sando, et al. Nonenzymatic DNA ligation in *Escherichia coli* cells. Nucleic Acids Res Suppl. 2002;(2):121-2.

Sando, et al. Quenched auto-ligating DNAs: multicolor identification of nucleic acids at single nucleotide resolution. J Am Chem Soc. Feb. 4, 2004;126(4):1081-7.

Silverman, et al. Quenched autoligation probes allow discrimination of live bacterial species by single nucleotide differences in rRNA. Nucleic Acids Res. Sep. 2, 2005;33(15):4978-86. Print 2005.

Skoog, et al. Pinciples of Instrumental analysis, 5th Ed., Harcourt Brace College Publishers (1998).

Soong, et al. Quantitative reverse transcription-polymerase chain reaction detection of cytokeratin 20 in noncolorectal lymph nodes. Clin Cancer Res. Nov. 2001;7(11):3423-9.

Sun, et al. Synthesis of 3'-thioribonucleosides and their incorporation into oligoribonucleotides via phosphoramidite chemistry. RNA. Nov. 1997;3(11):1352-63.

Sun, et al. Synthesis of 3'-Thioribouridine, 3'-Thioribocytidine, and Their Phosphoramidites, Nucleosides, Nucleotides, and Nucleic Acids. 2010; 16(7): 1543-1545.

Wiedmann, et al. Ligase chain reaction (LCR)—overview and applications. PCR Methods Appl. Feb. 1994;3(4):S51-64.

Xu, et al. High sequence fidelity in a non-enzymatic DNA autoligation reaction. Nucleic Acids Res. Feb. 1, 1999;27(3):875-81.

Xu, et al. Nonenzymatic autoligation in direct three-color detection of RNA and DNA point mutations. Nat Biotechnol. Feb. 2001;19(2):148-52.

Notice of Allowance dated Apr. 10, 2017 for U.S. Appl. No. 14/370,446.

Office Action dated Mar. 15, 2016 for U.S. Appl. No. 14/370,446.

Office Action dated Oct. 11, 2016 for U.S. Appl. No. 14/370,446.

\* cited by examiner

5-Octadiynyl dU (Alkyne)

Figure 15

| Oligo | Oligo Sequence | Modification | Position |
|---|---|---|---|
| ACR Primer 1 | GCTCCTCGTGGG/iFluorT/GAC/3AzideN/ | Azide | 3' |
| ACR Primer 2 | /5Hexynyl/G/i6-TAMN/ACGCTGGCGCCGGTC | Hexynyl Alkyne | 5' |
| Rev HEX Template | GGCAGCTCCTCGTGGGTGACGACGCTGGCGCCGGTCACCT | | |
| ACR Primer 3 | /5Hexynyl/GTCACCCACGAGGAGC | Hexynyl Alkyne | 5' |
| ACR Primer 4 | GACCGGGCGCCAGCGTC/3AzideN/ | Azide | 3' |
| Fwd HEX Template | AGGTGACCGGCGCCAGCGTCGTCACCCACGAGGAGCTGCC | | |
| ACR Primer 5 | TCGTGGG/iFluorT/GACGACGC/3AzideN/ | Azide | 3' |
| ACR Primer 6 | /5OCTdU/i6-TAMN/GGCGCCGGTCACCTC | Octadiynyl Alkyne | 5' |
| Rev OCT Template | CTCCTCGTGGGTGACGACGCTGGCGCCGGTCACCTCCTCG | | |
| ACR Primer 7 | /5OCTdU/CGTCACCCACGAGGA | Octadiynyl Alkyne | 5' |
| ACR Primer 8 | GTGACCGGGCGCCAGCG/3AzideN/ | Azide | 3' |
| Fwd OCT Template | CGAGGAGGTGACCGGCGCCAGCGTCGTCACCCACGAGGAG | | |

SEQUENCE LISTING

<160> NUMBER OF SEQ ID NOS: 16

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
<220> FEATURE:

```
<223> OTHER INFORMATION: 3'-SH

<400> SEQUENCE: 1
gcaacgaccg ttccgt                                                   16

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: 5'-BrAc
<220> FEATURE:
<221> NAME/KEY: modified_base
<222> LOCATION: (5)..(5)
<223> OTHER INFORMATION: T(FAM)

<400> SEQUENCE: 2
tcaatactgc gcagcc                                                   16

<210> SEQ ID NO 3
<211> LENGTH: 13
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: 3'-SH

<400> SEQUENCE: 3
ggctgcgcag tat                                                      13

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: 5'-BrAc

<400> SEQUENCE: 4
tgaacggaac ggtcgttgc                                                19

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(13)
<223> OTHER INFORMATION: iFluorT
<220> FEATURE:
<223> OTHER INFORMATION: 3'-3AzideN

<400> SEQUENCE: 5
gctcctcgtg ggtgac                                                   16

<210> SEQ ID NO 6
<211> LENGTH: 16
<212> TYPE: DNA
<213> ORGANISM: Artificial Sequence
```

```
<220> FEATURE:
<223> OTHER INFORMATION: Description of Artificial Sequence: Synthetic
      primer
<220> FEATURE:
<223> OTHER INFORMATION: 5'-5Hexynyl
<220> FEATURE:
<221> NAME/KEY: modified_base
<222> LOCATION: (1)..(1)
<223> OTHER INFORMATION: G(i6-TAMN)

<400> SEQUENCE: 6
gacgctggcg ccggtc                                                    16

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggcagctcct cgtgggtgac gacgctggcg ccggtcacct                          40

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: 5'-5Hexynyl

<400> SEQUENCE: 8
gtcacccacg aggagc                                                    16

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: 3'-3AzideN

<400> SEQUENCE: 9
gaccggcgcc agcgtc                                                    16

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aggtgaccgg cgccagcgtc gtcacccacg aggagctgcc                          40

<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
<220> FEATURE:
```

<221> NAME/KEY: modified_base
<222> LOCATION: (8)..(8)
<223> OTHER INFORMATION: iFluorT
<220> FEATURE:
<223> OTHER INFORMATION: 3'-3AzideN

<400> SEQUENCE: 11
tcgtgggtga cgacgc                                                      16

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (1)..(1)
<223> OTHER INFORMATION: 55OctdU(i6-TAMN)

<400> SEQUENCE: 12
uggcgccggt cacctc                                                      16

<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctcctcgtgg gtgacgacgc tggcgccggt cacctcctcg                            40

<210> SEQ ID NO 14
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (1)..(1)
<223> OTHER INFORMATION: 55OctdU

<400> SEQUENCE: 14
ucgtcaccca cgagga                                                      16

<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: 3'-3AzideN

<400> SEQUENCE: 15
gtgaccggcg ccagcg                                                      16

```
<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cgaggaggtg accggcgcca gcgtcgtcac ccacgaggag                            40
```

REAGENTS AND METHODS FOR AUTOLIGATION CHAIN REACTION

CROSS-REFERENCE

This application is a divisional of U.S. application Ser. No. 14/370,446, filed Jul. 2, 2014, now U.S. Pat. No. 9,725,761, issued Aug. 8, 2017, which is a National Stage Entry of International Application No. PCT/US2012/072192, filed Dec. 28, 2012, which claims the benefit of U.S. Provisional Patent Application No. 61/580,988, filed Dec. 28, 2011, each of which is entirely incorporated herein by reference.

STATEMENT AS TO FEDERALLY SPONSORED RESEARCH

This invention was made with government support under SBIR Phase I Award IIP-1046508 and SBIR Phase II Award IIP-1230464, both awarded by the National Science Foundation. The government has certain rights in the invention.

SEQUENCE LISTING

The instant application contains a Sequence Listing which has been submitted in ASCII format via EFS-Web and is hereby incorporated by reference in its entirety. Said ASCII copy, created on Feb. 8, 2013, is named 44086-701.601_SL.txt and is 4,714 bytes in size.

BACKGROUND OF THE INVENTION

Amplification of nucleic acid sequences is a widespread technology that has been used for many purposes, including diagnostic and forensic testing. Currently, this is carried out using polymerase chain reaction (PCR). Unfortunately, critical barriers exist with PCR that prevent both clinical and research labs from adopting PCR-based assays into a routine setting, due to bottlenecks with sample preparation and assay development costs. Specifically, PCR inhibitors, such as inhibitors to polymerases, found in many laboratory samples and clinical specimens cause low sensitivity and false-negative results in clinical and forensic tests that rely on PCR-based molecular techniques. Therefore, it is widely accepted that purification or pre-amplification of target DNA nucleic acids is required to remove or dilute out inhibitors prior to PCR amplification to obtain successful results. Optimization of PCR for genetic testing with different sample types can be labor-intensive, requiring extensive amounts of upfront development work, which in turn can significantly increase both the overall cost of a test and the time-to-result. See Al-Soud, W. A. & Rådström, P. (2001). Purification and Characterization of PCR-Inhibitory Components in Blood Cells. Journal of Clinical Microbiology, 39(2), 485-493; Huggett, J. F., Novak, T., Garson, J. A., Green, C., Morris-Jones, S. D., Miller, R. F. & Zumla, A. (2008). Differential susceptibility of PCR reactions to inhibitors: an important and unrecognised phenomenon. BMC Research Notes, 1(70), 1-9; Ochert, A. S., Boulter, A. W., Birnbaum, W., Johnson, N. W. & Teo, C. G. (1994). Inhibitory effect of salivary fluids on PCR: potency and removal. Genome Res., 3, 365-368; Ratnamohana, V. M., Cunningham, A. L., & Rawlinson, W. D. (1998). Removal of inhibitors of CSF-PCR to improve diagnosis of herpesviral encephalitis. Journal of Virological Methods, 72(1), 59-65; and Honoré-Bouakline, S., Vincensini, J. P., Giacuzzo, V., Lagrange, P. H. & Herrmann, J. L. (2003). Rapid Diagnosis of Extrapulmonary Tuberculosis by PCR: Impact of Sample Preparation and DNA Extraction. Journal of Clinical Microbiology, 41(6), 2323-2329.

With the upsurge in genetic information and the resultant increase in DNA biomarkers, researchers are now seeking new technologies to rapidly and cost-effectively interrogate this new information in a routine setting. However, the critical barriers associated with PCR make this technology too cost-prohibitive and too labor-intensive to use as a testing method for price-sensitive laboratories with limited resources and large numbers of samples.

Recently, technology has been developed to detect and monitor cellular genetic mutations using RNA-templated chemistry without amplification of the RNA template, in which chemically modified probes fluoresce when they hybridize to their genetic target in intact bacterial and human cells. See Franzini, R. M. and Kool, E. (2008). 7-Azidomethoxy-coumarins as profluorophores for template nucleic acid detection. Chem Bio Chem 9: 2981-2988; Franzini, R. M. and Kool, E. (2009). Efficient nucleic acid detection by template reductive quencher release. J. Am. Chem. Soc. 131: 16021-16023; Silverman, A. P. and Kool, E. (2005). Quenched autoligation probes allow discrimination of live bacterial species by single nucleotide differences in rRNA. Nucleic Acids Res. 33: 4978-4986; Sando, S. and Kool, E. (2002). Nonenzymatic DNA ligation in *Escherichia coli* cells. Nucleic Acids Res. Supplement No. 2: 121-122; Abe, H. and Kool., E. (2006). Flow cytometric detection of specific RNAs in native human cells with quenched autoligating FRET probes. Proc. Natl. Acad. Sci. USA 103: 263-268; Sengen Sun and Joseph A. Piccirilli. (2010). Synthesis of 3'-Thioribouridine, 3'-Thioribocytidine, and Their Phosphoramidites. Nucleosides, Nucleotides and Nucleic Acids. 16(7): 1543-1545.

This probe-based strategy, called quenched autoligation ("QUAL"), utilizes two self-reacting oligonucleotide probes that provide a fluorescence signal in the presence of fully complementary nucleic acid target sequence. A first oligonucleotide having a 3'-phosphoromono-thioate nucleophilic group anneals to a template target sequence, such that the 3'-phosphoromono-thioate nucleophilic group is juxtaposed to a 5'-electrophilic dabsylated group quencher of a second annealed oligonucleotide which has a fluorescein group quenched by the dabsyl group. This tandem configuration along a DNA template catalyzes the autoligation reaction, and joins the two oligonucleotides into a single probe. Upon ligation, the dabsyl quencher is displaced, and the fluoresceinyl fluorophore becomes un-quenched, resulting in an increase in fluorescence signal.

These short QUAL probes have been used to distinguish closely related bacterial species by discriminating single nucleotide differences in 16S rRNA sequences within live cells. However, QUAL is not compatible with in vitro applications that require the detection of small amounts of double-stranded nucleic acid sequences that are typically found in samples used for routine genetic testing of DNA biomarkers. For example, a QUAL in vitro reaction typically contains $10^{13}$ copies of single-stranded oligo DNA template, but a routine molecular assay can contain $10^3$ or fewer copies of dsDNA biomarkers—a ten billion-fold difference in copy-number detection. QUAL does not provide a way to amplify the signal resulting from the ligation reaction, because the product of the ligation reaction is a nucleic acid which is stably annealed to the template, thus occupying the template and not permitting it to participate in additional signal-generating reactions. Denaturing the reaction product from the template requires high temperatures at which the QUAL probes would be degraded. The autoligation chemistries used in QUAL have reduced stability at the high temperatures needed to separate double-stranded DNA.

There is, therefore, a need for methods, reagents, and kits for amplifying nucleic acid sequences without enzymes or nucleosides to enable cost-effective and easier-to-use alternatives for genetic testing that can be implemented in routine settings across multiple sample types without any sample-prep development.

BRIEF SUMMARY OF THE INVENTION

The invention relates to amplification of nucleic acid sequences. More particularly, the invention relates to amplification of nucleic acid sequences without enzymes or nucleosides. The invention provides reagents and methods for amplifying nucleic acid sequences without enzymes or nucleosides and effective at temperatures which denature nucleic acids.

The invention provides a method for amplifying a specific target nucleic acid sequence. In some embodiments, the invention provides a method for linearly amplifying a specific target nucleic acid sequence. In some embodiments, the invention provides a method for exponentially amplifying a specific target nucleic acid sequence. The method according to this aspect of the invention comprises contacting the target nucleic acid sequence with a first forward primer nucleic acid, a second forward primer nucleic acid, a first reverse primer nucleic acid and a second reverse primer nucleic acid under conditions wherein the primer nucleic acids specifically anneal with the target nucleic acid sequence. One forward primer nucleic acid has a first bond-forming reactive moiety and the other forward primer nucleic acid has a second bond-forming reactive moiety. One reverse primer nucleic acid has a first bond-forming reactive moiety and the other reverse primer nucleic acid has a second bond-forming reactive moiety. The first forward primer nucleic acid and the second forward primer nucleic acid are annealed to the target nucleic acid sequence such that the reactive moiety of the first forward primer nucleic acid and the reactive moiety of the second forward primer nucleic acid are juxtaposed. The first reverse primer nucleic acid and the second reverse primer nucleic acid are annealed to the target nucleic acid sequence such that the reactive moiety of the first reverse primer nucleic acid and the reactive moiety of the second reverse primer nucleic acid are juxtaposed. The reactive moiety of the first forward primer nucleic acid forms a chemical bond with the reactive moiety of the second forward primer nucleic acid to form a first ligation product, and the reactive moiety of the first reverse primer nucleic acid forms a chemical bond with the reactive moiety of the second reverse primer nucleic acid to form a second ligation product. Thus, the first ligation product forms a duplex with the target nucleic acid sequence and the second ligation product forms a duplex with the target nucleic acid sequence. The duplexes are then disrupted to form target nucleic acid sequences and the steps are repeated to amplify the target nucleic acid sequences. In some embodiments, the duplexes are thermally disrupted to form target nucleic acid sequences and the steps are repeated to amplify the target nucleic acid sequences.

In some embodiments, the ligation product formed by ligation of the forward or reverse primers does not comprise more than 1, 2, 3, 4, 5, or 6 bases which are not paired with the target nucleic acid sequence. For example, the ligation product formed by ligation of the forward or reverse primers does not comprise more than 2 bases which are not paired with the target nucleic acid sequence.

In some embodiments, a cycle consisting of steps (a) and (b) is performed in less than 2, 3, 4, 5, 6, 7, 8, 9 or 10 minutes. In some embodiments, the target nucleic acid sequence is present in the sample in a low copy number. For example, the sample comprises less than about $10^8$, $10^7$, $10^6$, $10^5$, $10^4$, $10^3$, $10^2$, or 10 copies.

In some embodiments, the first bond-forming reactive moiety is an azide and the second bond-forming reactive moiety is an alkyne. In some embodiments, the first bond-forming reactive moiety is an alkyne and the second bond-forming reactive moiety is an azide. In some embodiments, the target nucleic acid sequence is amplified exponentially. In other embodiments, the target nucleic acid sequence is amplified linearly.

In some embodiments, one forward or reverse primer nucleic acid comprises a dye or detectable group. In some embodiments, one forward or reverse primer nucleic acid comprises a fluorescence resonance energy transfer (FRET) donor fluorophore and/or the other forward or reverse primer nucleic acid comprises a FRET acceptor fluorophore, and the ligation products are detected by FRET. In some embodiments, the dye or detectable group is quenched by a quenching moiety in which annealing and autoligation separates the quenching moiety from the dye or detectable group before the ligated product is detected.

In some embodiments the forward and reverse primer nucleic acids contain neither a dye nor a detectable group, and the ligation products are detected by double-stranded nucleic acid binding dyes.

The invention further provides reagent compositions for amplifying a target nucleic acid sequence. In some embodiments, the invention provides reagent compositions for linearly amplifying a specific target nucleic acid sequence. In some embodiments, the invention provides reagent compositions for exponentially amplifying a specific target nucleic acid sequence. In some embodiments, a reagent composition according to the invention comprises a first forward primer nucleic acid having a thermally stable first bond-forming reactive moiety. In some embodiments, a reagent composition according to the invention comprises a second forward primer nucleic acid having a thermally stable second bond-forming reactive moiety. In some embodiments, a reagent composition according to the invention comprises a first reverse primer nucleic acid having a thermally stable first bond-forming reactive moiety. In some embodiments, a reagent composition according to the invention comprises a second reverse primer nucleic acid having a thermally stable second bond-forming reactive moiety. In such embodiments, the first bond-forming reactive moiety forms a chemical bond with the second bond-forming reactive moiety, when the first forward primer nucleic acid and the second forward primer nucleic acid are juxtaposed by annealing with a target nucleic acid and when the first reverse primer and the second reverse primer nucleic acid are juxtaposed by annealing with a target nucleic acid. In some embodiments, the first bond-forming reactive moiety is an alkyne (for example a hexynyl or octadiynyl group) and the second bond-forming reactive moiety is an azide. In some embodiments, the first bond-forming reactive moiety is an azide and the second bond-forming reactive moiety is an alkyne (for example a hexynyl or octadiynyl group). In some embodiments, one forward or reverse primer nucleic acid comprises a dye or detectable group. In some embodiments, one forward or reverse primer nucleic acid comprises a FRET donor fluorophore and/or the other forward or reverse primer nucleic acid comprises a FRET acceptor fluorophore. In some embodiments, the dye or detectable group is quenched by a quenching moiety in which annealing and autoligation separates the quenching moiety from the dye or detectable group before the ligated product is detected. In some embodiments the forward and reverse primer nucleic acids contain neither a dye nor a detectable group, and the ligation products are detected by double-stranded nucleic acid binding dyes.

Also provided are reaction mixtures comprising a reagent composition as described herein. In some embodiments, reaction mixtures comprise target nucleic acid sequences, including single-stranded and double-stranded target nucleic acid sequences. Reaction mixtures of the invention may further comprise any needed reagents, including buffers, salts, or dyes.

Provided herein is a kit for amplifying a target nucleic acid sequence. In some embodiments, the invention provides a kit for linearly amplifying a specific target nucleic acid sequence. In some embodiments, the invention provides a kit for exponentially amplifying a specific target nucleic acid sequence. The kit according to this aspect of the invention comprises a first forward primer nucleic acid, a second forward primer nucleic acid, a first reverse primer nucleic acid, and a second reverse primer nucleic acid. In the kit according to this aspect of the invention, the first forward primer nucleic acid, the second forward primer nucleic acid, the first reverse primer nucleic acid, and the second reverse primer nucleic acid are as described for the second aspect according to the invention. In some embodiments, the kit further comprises a second reagent composition as described herein, wherein the second reagent composition is designed for the amplification of at least a second target nucleic acid sequence. In some embodiments, the at least a second target nucleic acid sequence differs from the target nucleic acid sequence by at least a single nucleotide or nucleotide base pair, for example 1, 2, 3, 4 or more nucleotides or nucleotide base pairs.

Provided herein is also a method of detecting amplification of a nucleic acid target comprising: (a) contacting the target nucleic acid sequence with a first forward primer nucleic acid, a second forward primer nucleic acid, a first reverse primer nucleic acid and second reverse primer nucleic acid under conditions wherein the first and second forward primer nucleic acids specifically anneal with the target nucleic acid sequence and are juxtaposed on the target nucleic acid sequence; the first and second forward primer nucleic acids covalently ligate to each other upon binding to the target nucleic acid sequence, resulting in a first ligation product which forms a first duplex with the target nucleic acid sequence; the first and second reverse primer nucleic acids covalently ligate to each other upon binding to the target nucleic acid sequence, resulting in a first ligation product which forms a second duplex with the target nucleic acid sequence; (b) disrupting the duplex to release template target nucleic acid sequences and repeating step (a); and (c) during steps (a) or (b), detecting a change in a detectable signal, wherein the change is proportional to the amount of ligation products in the sample. For example, the signal is a fluorescent signal. In some embodiments, step (c) comprises determining an absolute or relative amount of target nucleic acid sequence. In some embodiments, the amplification is exponential. In some embodiments, the method is used in the amplification of at least a second target nucleic acid sequence, for example wherein the second target nucleic acid sequence differs from the target nucleic acid sequence by at least a single nucleotide or nucleotide base pair, for example by 1, 2, 3, 4 or more nucleotides or nucleotide base pairs.

Provided herein is a device for performing nucleic acid amplification of a target nucleic acid sequence, comprising: (a) an automated thermal cycler capable of alternately heating and cooling at least one reaction vessel comprising the reagent composition of the invention; (b) an excitation source for optically exciting the sample and causing the sample to fluoresce; and (c) a photodetector for detecting a fluorescent signal from the sample while the amplification reaction is in progress, which fluorescent signal is proportional to the amount of amplified nucleic acid in the reaction vessel.

Further provided is a method performing nucleic acid amplification of a first target nucleic acid sequence comprising: (a) mixing, in at least one reaction vessel, a dsDNA binding dye with a sample comprising a reagent composition of the invention and the first target nucleic acid sequence; (b) amplifying the first target nucleic acid sequence by alternately heating and cooling the reaction vessel; (c) detecting the fluorescence of the dsDNA binding dye by melting amplified target nucleic acid to generate a first melting curve; (d) repeating the mixing, amplifying and detecting steps with a second target nucleic acid sequence to generate a second melting curve; and (e) comparing the first and second melting curves to determine a difference in the nucleic acid composition of the first and second target nucleic acid sequences. In some embodiments, the difference is a single nucleotide or nucleotide base pair.

The invention further provides a device for performing nucleic acid amplification of a target nucleic acid sequence, comprising: (a) at least one reaction vessel comprising the reagent composition of the invention; (b) an excitation source for optically exciting the sample and causing the sample to fluoresce; (c) a photodetector for detecting temperature-dependent fluorescence levels from the sample; and (d) a processor programmed to generate a melting curve of the amplification product contained within the reaction vessel. For example, the device is configured to alternately heat and cool the reaction vessel.

Also provided is a method of amplifying of a target nucleic acid sequence comprising: (a) contacting the target nucleic acid sequence with a first forward primer nucleic acid and a second forward primer nucleic acid, under conditions wherein the first and second forward primer nucleic acids specifically anneal with the target nucleic acid sequence and are juxtaposed on the target nucleic acid sequence, wherein the first and second forward primer nucleic acids covalently bond upon binding to the target nucleic acid sequence, resulting in a ligation product which forms a duplex with the target nucleic acid sequence; and (b) disrupting the duplex to release the template target nucleic acid sequences and repeating step (a). In some embodiments, a cycle consisting of steps (a) and (b) is performed in less than 2, 3, 4, 5, 6, 7, 8, 9 or 10 minutes.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 15 shows ACR primer sequences (SEQ ID NOS 5-16, respectively, in order of appearance) containing an azide bond-forming reactive moiety (3AzideN),
and hexynyl (5Hexynyl) and octadiynyl (55 OCTdU) alkyne bond-forming reactive moieties to detect the maize Glutathione S-Transferase (GST) gene. Detection is through FRET using a fluorescein (iFluorT) and TAMRA (i6-TAMN) detection groups.

DETAILED DESCRIPTION OF THE INVENTION

Figure 1:
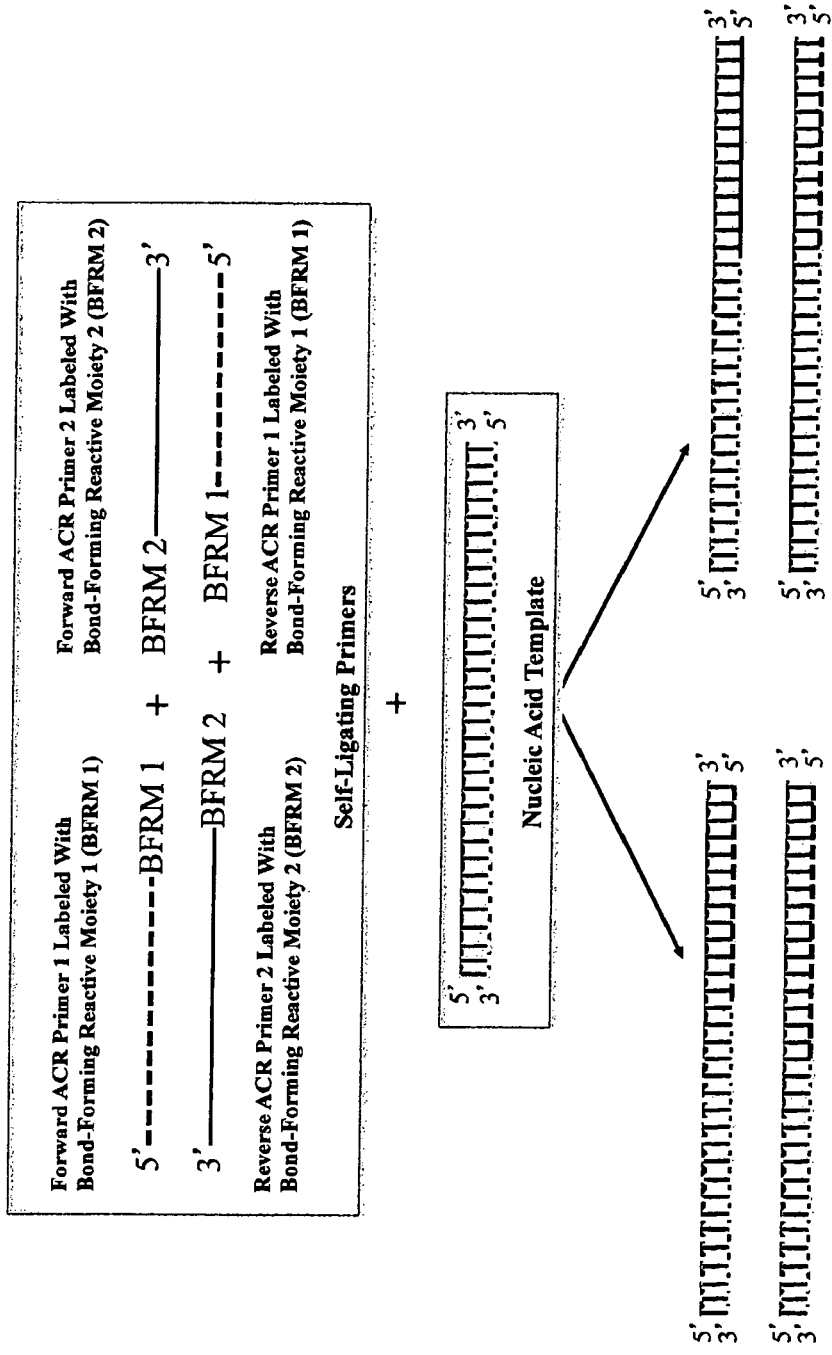
FIG. 1 illustrates the general strategy and expected results from two rounds of Autoligation Chain Reaction ("ACR"), in which four double-stranded products are generated from the amplification of a single nucleic acid target sequence. Various bond-forming reactive moieties (BFRM) can be used with ACR.

The invention relates to amplification of nucleic acid sequences. More particularly, the invention relates to amplification of nucleic acid sequences without enzymes or nucleosides. The invention provides reagents, methods, kits and devices for amplifying nucleic acid sequences without enzymes or nucleosides.

In one aspect, the invention provides a method for amplifying a specific target nucleic acid sequence. In some embodiments, the invention provides a method for linearly amplifying a specific target nucleic acid sequence. In some embodiments, the invention provides a method for exponentially amplifying a specific target nucleic acid sequence. The method according to this aspect of the invention comprises contacting the target nucleic acid sequence with a first forward primer nucleic acid, a second forward primer nucleic acid, a first reverse primer nucleic acid and a second reverse primer nucleic acid under conditions wherein the primer nucleic acids specifically anneal with the target nucleic acid sequence. One forward primer nucleic acid has a first bond-forming reactive moiety and the other forward primer nucleic acid has a second bond-forming reactive moiety. One reverse primer nucleic acid has a first bond-forming reactive moiety and the other reverse primer nucleic acid has a second bond-forming reactive moiety. In some embodiments, the first or second bond-forming reactive moiety are thermally stable, for example at temperatures capable of denaturing double-stranded nucleic acids. The first forward primer nucleic acid and the second forward primer nucleic acid are annealed to the target nucleic acid sequence such that the reactive moiety of the first forward primer nucleic acid and the reactive moiety of the second forward primer nucleic acid are juxtaposed. The first reverse primer nucleic acid and the second reverse primer nucleic acid are annealed to the target nucleic acid sequence such that the reactive moiety of the first reverse primer nucleic acid and the reactive moiety of the second reverse primer nucleic acid are juxtaposed. The reactive moiety of the first forward primer nucleic acid forms a covalent bond with the reactive moiety of the second forward primer nucleic acid to form a first ligation product, and the reactive moiety of the first reverse primer nucleic acid forms a covalent bond with the reactive moiety of the second reverse primer nucleic acid to form a second ligation product. Thus, the first ligation product forms a duplex with the target nucleic acid sequence and the second ligation product forms a duplex with the target nucleic acid sequence. The duplexes are then disrupted, for example by thermal denaturation, to form additional nucleic acid sequences which can serve as target nucleic acid sequences in the next cycle and the steps are repeated to thereby amplify the target nucleic acid sequences.

Template nucleic acid sequences can be single-stranded or double-stranded. If the template nucleic acid is single-stranded, in the first cycle of the amplification reaction only one of the pairs of primers (either the forward primers or reverse primers) will be able to bind to the template nucleic acid and form a duplexed ligation product. Upon disruption of the ligation product, the complement of the template nucleic acid will be present in the reaction mixture, thus allowing the other pair of primers to bind, such that all four primers are bound when the next cycle is initiated.

In some embodiments, the first bond-forming reactive moiety is a nucleophilic moiety and the second bond-forming reactive moiety is an electrophilic moiety. In some embodiments, the first bond-forming reactive moiety is an electrophilic moiety and the second bond-forming reactive moiety is a nucleophilic moiety. In some embodiments, the third bond-forming reactive moiety is a nucleophilic moiety and the fourth bond-forming reactive moiety is an electrophilic moiety. In some embodiments, the third bond-forming reactive moiety is an electrophilic moiety and the fourth bond-forming reactive moiety is a nucleophilic moiety. The nucleophilic or electrophilic moieties may be, for example, thermally stable.

In some embodiments, one forward or reverse primer nucleic acid comprises a dye or detectable group. In some embodiments, one forward or reverse primer nucleic acid comprises a FRET donor fluorophore and/or the other forward or reverse primer nucleic acid comprises a FRET acceptor fluorophore, and the ligation products are detected by FRET. In some embodiments, the dye or detectable group is quenched by a quenching moiety in which annealing and autoligation separates the quenching moiety from the dye or detectable group before the ligated product is detected.

In some embodiments the forward and reverse primer nucleic acids contain neither a dye nor a detectable group, and the ligation products are detected by double-stranded nucleic acid (e.g. dsDNA) binding dyes.

In a second aspect, the invention provides reagent compositions for amplifying a target nucleic acid sequence. In some embodiments, the invention provides reagent compositions for linearly amplifying a specific target nucleic acid sequence. In some embodiments, the invention provides reagent compositions for exponentially amplifying a specific target nucleic acid sequence. In some embodiments, a reagent composition according to the invention comprises a first forward primer nucleic acid having a first bond-forming reactive moiety. In some embodiments, a reagent composition according to the invention comprises a second forward primer nucleic acid having a second bond-forming reactive moiety. In some embodiments, a reagent composition according to the invention comprises a first reverse primer nucleic acid having a third bond-forming reactive moiety. In some embodiments, a reagent composition according to the invention comprises a second reverse primer nucleic acid having a fourth bond-forming reactive moiety. For example, the reactive moieties are thermally stable.

In some embodiments, the first bond-forming reactive moiety forms a chemical bond with the second bond-forming reactive moiety, when the first forward primer nucleic acid and the second forward primer nucleic acid are juxtaposed by annealing with a target nucleic acid and when the first reverse primer and the second reverse primer nucleic acid are juxtaposed by annealing with a target nucleic acid. In some embodiments, the first bond-forming reactive moiety is an alkyne (for example a hexynyl or octadiynyl group) and the second bond-forming reactive moiety is an azide. In some embodiments, the first bond-forming reactive moiety is an azide and the second bond-forming reactive moiety is an alkyne (for example a hexynyl or octadiynyl group). In some embodiments, one forward or reverse primer nucleic acid comprises a dye or detectable group. In some embodiments, one forward or reverse primer nucleic acid comprises a FRET donor fluorophore and/or the other forward or reverse primer nucleic acid comprises a FRET acceptor fluorophore. In some embodiments, the dye or detectable group is quenched by a quenching moiety in which annealing and autoligation separates the quenching moiety from the dye or detectable group before the ligated product is detected.

In some embodiments the forward and reverse primer nucleic acids contain neither a dye nor a detectable group, and the ligation products are detected by double-stranded nucleic acid binding dyes. For example, the reagent composition comprises a double-stranded nucleic acid (e.g. dsDNA) binding dye.

In a third aspect, the invention provides a kit for amplifying a target nucleic acid sequence. In some embodiments, the invention provides a kit for linearly amplifying a specific target nucleic acid sequence. In some embodiments, the invention provides a kit for exponentially amplifying a specific target nucleic acid sequence. The kit according to this aspect of the invention comprises a first forward primer nucleic acid, a second forward primer nucleic acid, a first reverse primer nucleic acid, and a second reverse primer nucleic acid. In the kit according to this aspect of the invention, the first forward primer nucleic acid, the second forward primer nucleic acid, the first reverse primer nucleic acid, and the second reverse primer nucleic acid are as described for the second aspect according to the invention.

Non-limiting examples of reagents and methods according to the invention are shown in FIGS. 1, 2, 4, and 5, which illustrate the strategy and expected results from two rounds of ACR, in which four double-stranded products are generated from the amplification of a single target sequence. Forward ACR Primer 1 and Reverse ACR Primer 1 both contain a bond-forming reactive moiety at the 3' end. Forward ACR Primer 2 and Reverse ACR Primer 2 both contain a bond-forming reactive moiety at the 5' end. When forward and reverse primers are annealed in tandem to template, the juxtaposition of the bond-forming reactive moieties results in a DNA-templated autoligation reaction without any enzymes or nucleotides. Primers annealed in tandem have higher melting temperature due to stabilizing base-pair stacking interactions between the tandemly-aligned oligos. See Lane, M. J., Paner, T., Kashin, I., Faldasz, B. D., Li, B., Gallo, F. J. & Benight, A. S. (1997). The thermodynamic advantage of DNA oligonucleotide 'stacking hybridization' reactions: energetics of a DNA nick. Nucleic Acids Research, 25(3), 611-617. ACR can be performed at annealing temperatures that favor the formation of primer/template heteroduplexes over primer dimers in homoduplexes. The resulting autoligation products are used as templates in subsequent rounds of amplification.

Non-limiting examples of bond-forming reactive moieties include moieties which participate in cycloaddition reactions, including azides and alkynes which participate in 'click' cycloaddition reactions. Other examples of possible bond-forming reactive moieties include thiol nucleophilic and bromoacetate electrophilic moieties, which are common generic chemistries that are commercially available. The preparation, protocol, and application of the 3'-thionucleoside thiol as a thermal-stable nucleophile are well documented in the literature. See, for example, Ghalia Sabbagh, Kevin J. Fettes, Rajendra Gosain, Ian A. O'Neil and Richard Cosstick (2004). Synthesis of phosphorothioamidites derived from 3'-thio-3'-deoxythymidine and 3'-thio-2',3'-dideoxycytidine and the automated synthesis of oligodeoxynucleotides containing a 3'-S-phosphorothiolate linkage. Nucleic Acids Research, 32(2) 495-501; Meena, Mui Sam, Kathryn Pierce, Jack W. Szostak, and Larry W. McLaughlin. (2',3'-Dideoxy-3'-Thionucleoside Triphosphates: Syntheses and Polymerase Substrate Activities. Supporting Information; Miller, G. P., Silverman, A. P. & Kool, E. (2008). New, stronger nucleophiles for nucleic acid-templated chemistry: Synthesis and application in fluorescence detection of cellular RNA. Bioorganic & medicinal chemistry, 16(1), 56-64; Meena, Mui Sam, Kathryn Pierce, Jack W. Szostak, and Larry W. McLaughlin. (2007). (2',3'-Dideoxy-3'-Thionucleoside Triphosphates: Syntheses and Polymerase Substrate Activities. Organic Letters. 9(6): 1161-1163; and Sengen Sun, Aiichiro Yoshids, and Joseph A. Piccirilli. (1997). Synthesis of 3'-thioribonucleosides and their incorporation into oligoribonucleotides via phosphoramidite chemistry. RNA. 3: 1352-1363.

Figure 12:
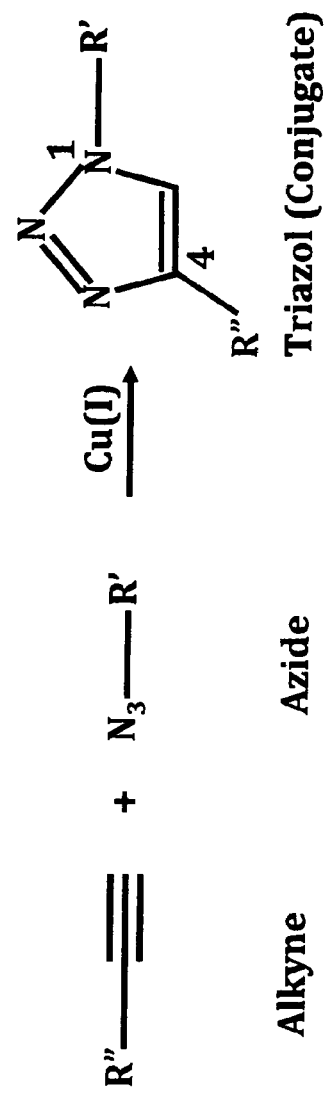
FIG. 12 shows a non-limiting example of an ACR bond-forming chemistry through cycloaddition with alkyne and azide moieties to generate a covalent carbon-heteroatom bond between species to form a triazol conjugate.
Figure 13:
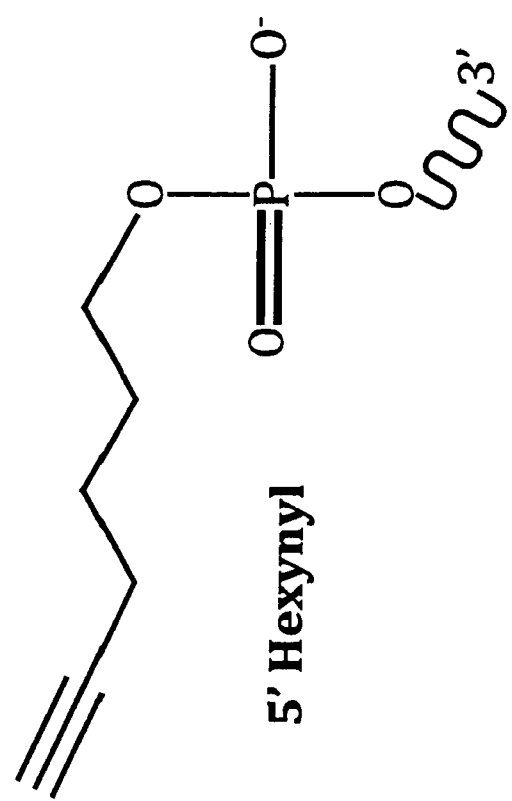
FIG. 13 shows a non-limiting example of a bond-forming reactive moiety using a hexynyl alkyne modification. This can be used to conjugate an ACR Primer 2 to an ACR Primer 1 modified with an azide bond-forming reactive moiety.
Figure 14:
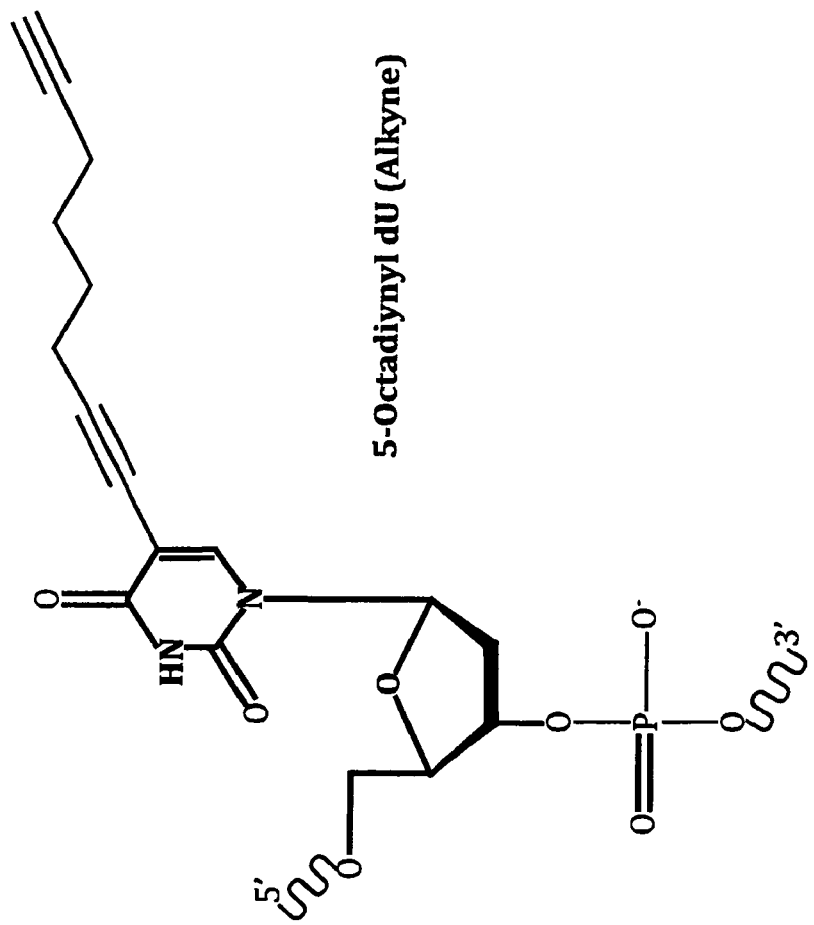
FIG. 14 shows a non-limiting example of a bond-forming reactive moiety using an octadiynyl alkyne modification. This can be used to conjugate an ACR Primer 2 to an ACR Primer 1 modified with an azide bond-forming reactive moiety.

FIGS. 12-14 illustrate other non-limiting examples of bond-forming reactive moieties that include hexynyl and octadiynyl alkynes to conjugate with an azide bond-forming reactive moiety using cycloaddition chemistries to generate a covalent carbon-heteroatom bond between species to form a triazol conjugate.

FIG. 15 illustrates non-limiting examples ACR primer sequences containing an azide bond-forming reactive moiety (3AzideN), and hexynyl (5Hexynyl) and octadiynyl (55OCTdU) alkyne bond-forming reactive moieties using a fluorescein (iFluorT) and TAMRA (i6-TAMN) detection groups in FRET for detection. This illustrates that a variety of chemistries with auto-reactive moieties are available for ACR.

Non-limiting examples of bond-forming nucleophilic moieties include azides, cyclooctyne, phosphorodithioate, phosphorotrithioate, 2',3'-cyclic phosphate, amino-deoxyribonucleosides, thiol, amino, hydrazine, and hydrazide. Non-limiting examples of bond-forming electrophilic moieties include alkynes, tetrazine, bromide, iodide, chloride, maleimide, dabsylate, disulfides, tosylate, isothiocyanate, NHS ester, imidoester, PFP ester, alkyl azide, aryl azide, isocyanate, nitrophenyl mono- or di-ester, aldehyde, and epoxy.

Forward ACR Primer 1 and Reverse ACR Primer 2 and Forward ACR Primer 2 and Reverse ACR Primer 1 are complementary pairs, which increase the specificity of the reaction by sequestering the primers in duplexes until dsDNA templates outcompete the formation of primer homoduplexes by annealing to the primers. Because tandemly-annealed oligos on a template have significantly higher melting temperatures than individual oligos annealed to the same template, due to stabilizing base-pair stacking interactions between the tandemly-aligned oligos, ACR can be performed at annealing temperatures that favor the formation of primer/template heteroduplexes over homoduplexed primer sets.

For purposes of the invention, a "primer nucleic acid" is an oligonucleotide used in the method according to the invention to form a longer oligonucleotide via autoligation to another primer nucleic acid. Primer nucleic acids may be from about 5 to about 35 nucleotides in length, for example from about 5 to about 25, about 5 to about 20, about 5 to about 18, or about 10 to about 18 nucleotides. The autoligation reaction occurs when the primer nucleic acids are annealed to a target nucleic acid sequence such that a first bond-forming reactive moiety of one primer nucleic acid is juxtaposed with a second bond-forming reactive moiety of another primer nucleic acid. In some embodiments the first bond-forming reactive moiety is at a terminus (5' or 3') of one primer nucleic acid and the second bond-forming reactive moiety is at an opposite terminus of the other primer nucleic acid. The terms "first bond-forming reactive moiety" and "second bond-forming reactive moiety" refer to chemical functional groups that are capable of reacting with each other to form a covalent bond.

Non-limiting examples of first bond-forming reactive moieties include azides, cyclooctyne, phosphorodithioate, phosphorotrithioate, 2',3'-cyclic phosphate, amino-deoxyribonucleosides, thiol, amino, hydrazine, and hydrazide. In some embodiments, the first bond-forming reaction is an azide. In certain embodiments, the first bond-forming reactive moiety is a nucleophile. In some embodiments, the 3' terminal nucleophile is a 3'-thionucleoside.

Non-limiting examples of second bond-forming reactive moieties include alkynes, tetrazine, bromide, iodide, chloride, maleimide, dabsylate, disulfides, tosylate, isothiocyanate, NHS ester, imidoester, PFP ester, alkyl azide, aryl azide, isocyanate, nitrophenyl mono- or di-ester, aldehyde, and epoxy. In some embodiments, the second bond-forming reactive moiety is an alkyne, for example an octadiynyl or hexynyl group. In certain embodiments, the second bond-forming reactive moiety is an electrophile. In some embodiments, the 5'-terminal electrophile is a 5'-bromoacetyl-nucleoside.

Amplification of a double-stranded target nucleic acid sequence requires disruption of duplex target sequence. In some embodiments, disruption occurs by thermally denaturing double-stranded target nucleic acid sequence by raising the temperature above the melting temperature.

Reaction efficiency is enhanced when the bond-forming moieties used are thermally stable. In this context, the term "thermally stable" means that the reactivity of a bond-forming moiety is not destroyed or functionally compromised to such an extent that the desired reaction no longer occurs with sufficient efficiency at temperatures required to denature the target sequence.

In some embodiments, a dye or detectable group is used to detect the ligated products formed by annealing and autoligation. Non-limiting dyes and detectable groups include, without limitation, the groups shown in Table I below.

TABLE I

| Detectable Dyes and Groups |
| --- |
| (E)-Stilbene |
| (Z)-Stilbene |
| 1-Chloro-9,10-bis(phenylethynyl)anthracene |
| 2-Chloro-9,10-bis(phenylethynyl)anthracene |
| 2-Chloro-9,10-diphenylanthracene |
| 5,12-Bis(phenylethynyl)naphthacene |
| 7-Aminoactinomycin D |
| 7-Aminoactinomycin D (7-AAD) |
| 7-Hydroxy-4-methylcoumarin |
| 8-Anilinonaphthalene-1-sulfonate |
| 9,10-Bis(phenylethynyl)anthracene |
| Acridine orange |
| Acridine yellow |
| Alexa Fluor |
| Alexa Fluor 350 dye, 7-amino-4-methylcoumarin (AMC) |
| Alexa Fluor 405 dye |
| Alexa Fluor 430 dye |
| Alexa Fluor 488 dye |
| Alexa Fluor 514 dye |
| Alexa Fluor 532 dye |
| Alexa Fluor 546 dye |
| Alexa Fluor 555 dye |
| Alexa Fluor 568 dye |
| Alexa Fluor 594 dye |
| Alexa Fluor 610 dye |
| Alexa Fluor 633 dye |
| Alexa Fluor 635 dye |
| Alexa Fluor 647 dye |
| Alexa Fluor 660 dye |
| Alexa Fluor 680 dye |
| Alexa Fluor 700 dye |
| Alexa Fluor 750 dye |
| Alexa Fluor 790 dye |
| Allophycocyanin |
| ATTO dyes |
| Auramine-rhodamine stain |
| BCECF indicator |
| Benzanthrone |
| BHQ-1 |
| BHQ-2 |
| BHQ-3 |
| Bimane |

TABLE I-continued

| Detectable Dyes and Groups |
| --- |
| Blacklight paint |
| blue fluorescent proteins |
| BOBO-1, BO-PRO-1 |
| BODIPY 630/650 dye |
| BODIPY 650/665 dye |
| BODIPY dye |
| BODIPY FL dye |
| BODIPY TMR-X dye |
| BODIPY TR-X dye |
| Brainbow |
| Calcein |
| Calcium Crimson indicator |
| Calcium Green indicators |
| Calcium Orange indicator |
| Carboxy SNARF indicators |
| Carboxyfluorescein |
| Carboxyfluorescein diacetate succinimidyl ester |
| Carboxyfluorescein succinimidyl ester |
| Cascade Blue dye |
| Cascade Yellow dye |
| Chemiluminescent |
| Colorimetric |
| Coumarin |
| Cy-3 |
| Cy-5 |
| Dabcyl |
| DAPI |
| Dark quencher |
| DDQ-I |
| DDQ-II |
| Di-8-ANEPPS, Di-4-ANEPPS |
| DiA |
| DiD (DiIC18(5)) |
| DiI (DiIC18(3)) |
| DiO (DiOC18(3)) |
| DiOC6 |
| DiR (DiIC18(7)) |
| DyLight Fluor |
| Eclipse |
| ELF 97 alcohol |
| Eosin |
| ER Tracker Blue-White DPX |
| EthD-1 |
| Ethidium bromide |
| excimer/exciplex partner |
| exciplex dyes |
| FAM |
| Fluo-3 indicator |
| Fluo-4 |
| Fluo-4 indicator |
| FluoProbes |
| Fluorescein |
| Fluorescein isothiocyanate |
| Fluorescein, FITC |
| Fluoro-Jade stain |
| fluorophore-quencher couples, |
| FM 1-43, FM 1-43FX |
| FM 4-64, FM 4-64FX |
| Fura Red indicator |
| Fura-2 indicator |
| Fura-2-acetoxymethyl ester |
| gold nano particles |
| Green fluorescent protein |
| HEX |
| Hoechst 33258, Hoechst 33342 |
| Indian yellow |
| Indo-1 |
| inorganic quantum dots |
| Iowa Black FQ |
| Iowa Black RQ |
| JC-1 |
| JC-9 |
| JOE |
| LC red 640 |
| LC red 705 |
| Lissamine rhodamine B |
| Lucifer yellow |
| Lucifer yellow CH |

TABLE I-continued

Detectable Dyes and Groups

Luciferin
LysoSensor Blue DND-167
LysoSensor Green DND-153, DND-189
LysoSensor Yellow/Blue DND-160 (PDMPO)
LysoTracker Green
LysoTracker Red
Magnesium Green indicator
Marina Blue dye
Merocyanine
MGB groups
MitoTracker Green FM
MitoTracker Orange CMTMRos
MitoTracker Red CMXRos
Monobromobimane
NBD amines
NED
NeuroTrace 500/525 green-fluorescent Nissl stain
Nile blue
Nile red
Optical brightener
Oregon Green 488 dye and Oregon Green 488 BAPTA
Oregon Green 514 dye
Pacific Blue dye
Pacific Orange dye
Perylene
Phloxine
Phycobilin
Phycoerythrin
Phycoerythrobilin
POPO-1, PO-PRO-1
Propidium iodide
Pyranine
QSY-21
QSY-7
R-phycoerythrin
red fluorescent proteins
Resorufin
RH 414
Rhod-2 indicator
Rhodamine
Rhodamine 110
Rhodamine 123
Rhodamine 123
Rhodamine 6G
Rhodamine Green dye
Rhodamine Red dye
RiboGreen
RoGFP
ROX
Rubrene
SERRS-active fluorescence dyes
Sodium Green indicator
Sulforhodamine 101
Sulforhodamine B
SYBR Green
Synapto-pHluorin
SYTO blue-fluorescent nucleic acid stains 40, 41,
SYTO blue-fluorescent nucleic acid stains 44, 45
SYTO green-fluorescent nucleic acid stains 11, 14, 15, 20,
SYTO green-fluorescent nucleic acid stains 12, 13, 16, 21,
SYTO orange-fluorescent nucleic acid stains 80, 81, 82,
SYTO orange-fluorescent nucleic acid stains 84,
SYTO red-fluorescent nucleic acid stains 17, 59,
SYTO red-fluorescent nucleic acid stains 60, 62,
SYTOX Blue nucleic acid stain
SYTOX Green nucleic acid stain
SYTOX Orange nucleic acid stain
TAMRA
TET
Tetramethylrhodamine, Rhodamine B
Tetraphenyl butadiene
Tetrasodium tris(bathophenanthroline
Texas Red
Texas Red-X dye
Titan yellow
TMR
TOTO-1, TO-PRO-1
TOTO-3, TO-PRO-3

TABLE I-continued

Detectable Dyes and Groups

TSQ
Umbelliferone
X-rhod-1 indicator
Yellow fluorescent protein
YOYO-1, YO-PRO-1
YOYO-3, YO-PRO-3

In some embodiments, the first forward primer and second forward primer or the first reverse primer are conjugated to dyes that are, respectively, a donor dye and an acceptor dye for FRET. Alternatively, the first forward primer and second forward primer or the first reverse primer are conjugated to dyes that are, respectively, an acceptor dye and a donor dye for FRET. Alternatively, the donor and acceptor dyes for FRET may be, respectively, on the second reverse primer and the first reverse primer or the second forward primer. Alternatively, the second reverse primer and the first reverse primer or the second forward primer are conjugated to dyes that are, respectively, an acceptor dye and a donor dye for FRET. Alternatively, the first forward primer and second forward primer are conjugated to dyes that are, respectively, an acceptor dye and a donor dye, and the second reverse primer and the first reverse primer are conjugated to dyes that are, respectively, an acceptor dye and a donor dye for FRET. Alternatively, the first forward primer and second forward primer are conjugated to dyes that are, respectively, a donor dye and an acceptor dye, and the second reverse primer and the first reverse primer are conjugated to dyes that are, respectively, a donor dye and an acceptor dye for FRET. In some embodiments, the donor and acceptor dyes are spaced from about 1 to about 20 nucleotides apart within the autoligation product, for example within about 1 to about 15, about 1 to about 10, about 1 to about 5, or about 1 to about 3 nucleotides. In some embodiments, the donor dye is FAM and the acceptor dye is Texas Red.

In some embodiments, the dye or detectable group is quenched by a quenching moiety in which annealing and autoligation separates the quenching moiety from the dye or detectable group before the ligated product is detected.

In some embodiments the forward and reverse primer nucleic acids contain neither a dye nor a detectable group, and the ligation products are detected by double-stranded nucleic acid binding dyes.

In some embodiments, a method of the invention is used to detect the presence or absence of a mutation, for example a SNP mutation, in a biological sample. Generally, the test sample can be biological and/or environmental samples. Biological samples may be derived from human, other animals, or plants, body fluid, solid tissue samples, tissue cultures or cells derived therefrom and the progeny thereof, sections or smears prepared from any of these sources, or any other samples suspected to contain the target nucleic acids. Biological samples include body fluids including but not limited to blood, urine, spinal fluid, cerebrospinal fluid, sinovial fluid, amniotic fluid, semen, and saliva. Other types of biological sample may include food products and ingredients such as vegetables, dairy items, meat, meat by-products, and waste. Biological samples also include plant tissue such as seed or leaf tissue. Environmental samples are derived from environmental material including but not limited to soil, water, sewage, cosmetic, agricultural and industrial samples.

In some embodiments, a method of the invention is used to perform high resolution melt curve analysis (HRM). DNA melt curve analysis can reveal the number of DNA species or purity of an amplification reaction, and thus is often used as a more convenient alternative to gel electrophoresis to confirm the specificity of ACR. According to one embodiment, the nucleic acid detection is associated with high resolution melt curve analysis (HRM). Compared to regular DNA melt curve analysis, HRM can yield more information on the amplified DNA product, including the capability for point mutation detection (SNP), zygosity testing and epigenetics analysis. Like regular DNA melt curve analysis, HRM is a post-ACR product analysis method. In HRM, a target nucleic acid is first amplified by ACR in the presence of a DNA binding dye and then the PCR product-dye complex is slowly melted as the fluorescence change is monitored to generate a standard DNA melt curve. The procedure is repeated with additional target nucleic acid(s) to generate additional melt curve(s). The additional melt curve(s) are compared with the standard curve to yield minor differences that may be indicative of mutation site(s) in the target nucleic acid sequences (U.S. Pat. Nos. 7,387,887; 7,456,281; and 7,582,429).

The invention provides for systems that can be used to detect target analytes, such as nucleic acids. The system can include at least one detector (e.g., a spectrometer, etc.) that detects a signal that is indicative of a target analyte. For example, the system can include a detector for measuring an optical signal, such as fluorescence. In addition, the system can include at least one thermal modulator (e.g., a thermal cycling device, etc.) operably connected to a container or solid support to modulate temperature of a sample. The thermal modulator can be used for performing nucleic acid amplification methods, melting curve analysis, and/or hybridization assays.

Detectors can be structured to detect detectable signals produced, e.g., in or proximal to another component of the given assay system (e.g., in container, on a solid support, etc.). Suitable signal detectors that are optionally utilized, or adapted for use, herein detect, e.g., fluorescence, phosphorescence, radioactivity, absorbance, refractive index, luminescence, mass, or the like. Detectors optionally monitor one or a plurality of signals from upstream and/or downstream of the performance of, e.g., a given assay step. For example, detectors optionally monitor a plurality of optical signals, which correspond to real-time events. Example detectors or sensors include photomultiplier tubes, CCD arrays, optical sensors, temperature sensors, pressure sensors, pH sensors, conductivity sensors, scanning detectors, or the like. More specific exemplary detectors that are optionally utilized in performing the methods of the invention include, e.g., resonance light scattering detectors, emission spectroscopes, fluorescence spectroscopes, phosphorescence spectroscopes, luminescence spectroscopes, spectrophotometers, photometers, and the like. Detectors are also described in, e.g., Skoog et al., *Principles of Instrumental Analysis*, 5$^{th}$ Ed., Harcourt Brace College Publishers (1998) and Currell, *Analytical Instrumentation: Performance Characteristics and Quality*, John Wiley & Sons, Inc. (2000), both of which are incorporated by reference.

The systems of the invention can include controllers that are operably connected to one or more components (e.g., detectors, thermal modulators, fluid transfer components, etc.) of the system to control operation of the components. More specifically, controllers can be included either as separate or integral system components that are utilized, e.g., to receive data from detectors, to effect and/or regulate temperature in the containers, to effect and/or regulate fluid flow to or from selected containers, or the like. Controllers and/or other system components is/are optionally coupled to an appropriately programmed processor, computer, digital device, or other information appliance (e.g., including an analog to digital or digital to analog converter as needed), which can function to instruct the operation of these instruments in accordance with preprogrammed or user input instructions, receive data and information from these instruments, and interpret, manipulate and report this information to the user. Controllers are available from various commercial sources.

Any controller or computer optionally includes a monitor, which is often a cathode ray tube ("CRT") display, a flat panel display (e.g., active matrix liquid crystal display, liquid crystal display, etc.), or others. Computer circuitry is often placed in a box, which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user.

The computer can include appropriate software for receiving user instructions, either in the form of user input into a set of parameter fields, e.g., in a GUI, or in the form of preprogrammed instructions, e.g., preprogrammed for a variety of different specific operations. The software then converts these instructions to appropriate language for instructing the operation of one or more controllers to carry out the desired operation. The computer then receives the data from, e.g., sensors/detectors included within the system, and interprets the data, either provides it in a user understood format, or uses that data to initiate further controller instructions, in accordance with the programming, e.g., such as controlling fluid flow regulators in response to fluid weight data received from weight scales or the like.

In some embodiments, the invention provides integrated systems for performing ACR and for making $T_m$ determinations. The systems can include instrumentation and tools for interpreting and analyzing collected data, especially including tools for determining quantity of amplified nucleic acids and for deriving $T_m$. These tools can include algorithms and/or the ability to electronically store information (e.g., collected fluorescence data, predetermined $T_m$ correlations, etc). Each part of an integrated system can be functionally interconnected, and in some cases, physically connected. In some embodiments, the integrated system is automated, where there is no requirement for any manipulation of the sample or instrumentation by an operator following initiation of the ACR or $T_m$ analysis.

A system of the invention can include instrumentation. For example, the invention can include a detector such as a fluorescence detector (e.g., a fluorescence spectrophotometer). A detector or detectors can be used in conjunction with the invention, e.g., to monitor/measure the emission from a light emitting moiety, such as a nucleic acid dye. A detector can be in the form of a multiwell plate reader to facilitate the high-throughput capacity of the assays described herein.

In some embodiments, the integrated system includes a thermal cycling device, or thermocycler, for the purpose of controlling the temperature of the $T_m$ melting analysis or for modulating the temperature for performing nucleic acid amplification. In some embodiments, the thermal cycling device and the detector are an integrated instrument, where the thermal cycling and emission detection (e.g., fluorescence detection) are performed in the same device.

A detector, e.g., a fluorescence spectrophotometer, can be connected to a computer for controlling the spectrophotometer operational parameters (e.g., wavelength of the excitation and/or wavelength of the detected emission) and/or for storage of data collected from the detector (e.g., fluorescence measurements during a melting curve analysis). The computer may also be operably connected to the thermal cycling device to control the temperature, timing, and/or rate of temperature change in the system. The integrated computer can also contain the "correlation module" where the data collected from the detector is analyzed and where the $T_m$ of the target hybridization complex and/or the concentration of amplified or target nucleic acid is determined. In some embodiments, the correlation module comprises a computer program that calculates the $T_m$ or the concentration of nucleic acid based on the fluorescence readings from the detector, and in some cases, optionally derives sequence and/or genotype information of an unknown sample based on the $T_m$ and/or ACR result. In some embodiments, the correlation module compares the $T_m$ of the unknown sample with a database (or table) of $T_m$ values for known sequences and/or genotypes to make a correlation between the $T_m$ of the unknown sample and the sequence or genotype of the unknown sample.

In some aspects, a system of the invention for the determination of a $T_m$ of a hybridization complex and/or for performing ACR comprises a reagent composition, a thermal control device for regulating the temperature reaction over a range of temperatures, and a detector for measuring the signal from the melting reaction over the range of temperatures. In some cases, the system also includes a correlation module that is operably coupled to the detector and receives signal measurements, where the correlation module correlates the signal intensity with the concentration of the target analyte or the melting temperature of the target analyte.

The following examples are intended to further illustrate certain embodiments of the invention and are not to be construed to limit the scope of the invention.

Example 1

ACR Amplification Method

The method and expected results from two rounds of ACR, in which four double-stranded products are generated from the amplification of a single nucleic acid target sequence are shown (FIG. 1). Forward ACR Primer 1 and Reverse ACR Primer 1 are both labeled with a first bond-forming reactive moiety at the 3' end (BFRM 1). Forward ACR Primer 2 and Reverse ACR Primer 2 are both labeled with a second bond-forming reactive moiety at the 5' end (BFRM 2). When forward and reverse primers are annealed in tandem to template, the juxtaposition of the first and second bond-forming reactive moieties results in a nucleic acid-templated autoligation reaction without any enzymes or nucleotides. Primers annealed in tandem have higher melting temperature due to stabilizing base-pair stacking interactions between the tandemly-aligned oligos. See Lane, M. J., Paner, T., Kashin, I., Faldasz, B. D., Li, B., Gallo, F. J. & Benight, A. S. (1997). The thermodynamic advantage of DNA oligonucleotide 'stacking hybridization' reactions: energetics of a DNA nick. Nucleic Acids Research, 25(3), 611-617. ACR can be performed at annealing temperatures that favor the formation of primer/template heteroduplexes over primer dimers in homoduplexes. The resulting autoligation products are used as templates in subsequent rounds of amplification to generate exponential growth of double-stranded products. A variety of bond-forming reactive moieties can be used with the methods described herein, which are not limited to any specific bond-forming chemistry.

Example 2

ACR Detection with Dyes

Figure 2:
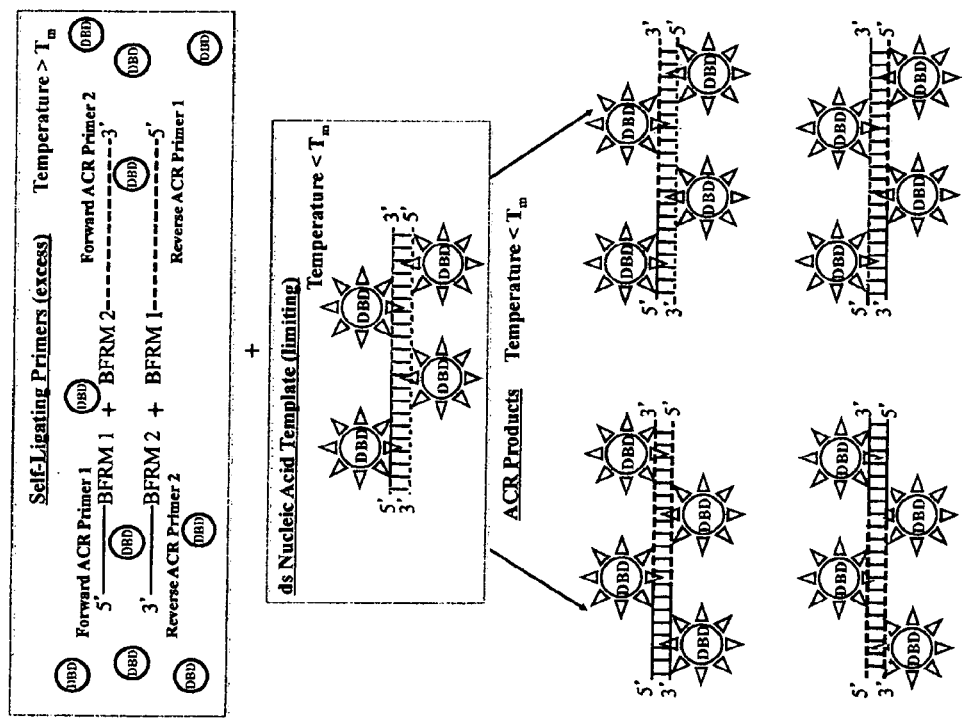
FIG. 2 illustrates the strategy and expected results from two rounds of ACR, in which four double-stranded products are generated from the amplification of a single nucleic acid target sequence, and detection with double-stranded nucleic acid binding dyes (DBD). Different dyes can be used with ACR.

An example using detection dyes and expected results from two rounds of ACR, in which four double-stranded products are generated from the amplification of a single nucleic acid target sequence are shown, and detection with double-stranded nucleic acid binding dyes (DBD) (FIG. 2). The resulting autoligation products are detected by DBDs when double-stranded. In this example, detection by DBD binding to double-stranded nucleic acids is achieved at temperatures below (<) the melting temperature ($T_m$) of the ACR products and above (>) the $T_m$ of the self-ligating ACR primers. A variety of bond-forming reactive moieties can be used with the methods described herein, which are not limited to any specific bond-forming chemistry.

Example 3

ACR Detection with SYBR Green I in Real-Time

Figure 3:
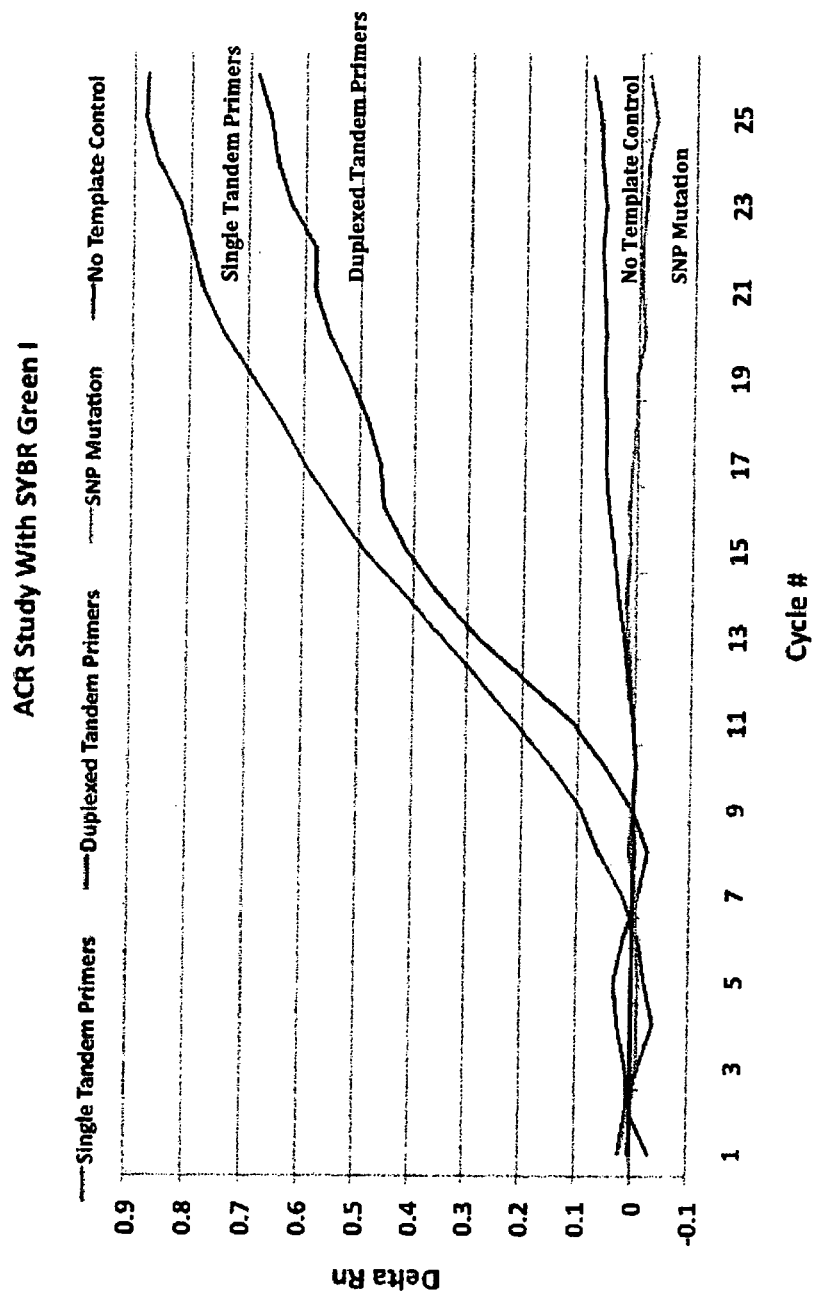
FIG. 3 shows ACR self-ligation reactions with dsDNA nucleic acid template using duplexed tandem primers or single tandem primers and SYBR Green I for detection of binding to the duplexes formed from amplification reactions in the presence or absence of a single nucleotide polymorphism (SNP) mutation. This illustrates that ACR has the specificity to detect SNPs.

The results of ACR self-ligation reactions using a dye with dsDNA nucleic acid template using duplexed tandem primers or single tandem primers and SYBR Green I for detection of binding to the duplexes formed from amplification reactions in the presence or absence of a SNP mutation (FIG. 3). Each trace represents an average of 4 replicates measured across 26 cycles. Each reaction contained a 1000-fold molar excess of self-ligating primers over a dsDNA primer template. SYBR Green I binding to duplexes formed between the autoligation products and complementary strands of template DNA was used to monitor the increase in double-stranded amplification products from a single pair of ACR primers ("Single Tandem Primers"), or a pair of ACR primers with their complementary primers ("Duplexed Tandem Primers"). Template carrying a SNP mutation ("SNP Mutation") was used to determine the specificity of the reaction. Omitted template ("No Template Control") was used as a negative control for the reaction.

Reactions were performed using the strategy shown in FIG. 2, using 7-mers (Forward ACR Primer 1 and Reverse ACR Primer 2) and 13-mers (Forward ACR Primer 2 and Reverse ACR Primer 1). Forward ACR Primer 1 and Reverse ACR Primer 1 contain a phosphoromono-thioate ester nucleophile (BFRM 1) at the 3'-terminus, while Forward ACR Primer 2 and Reverse ACR Primer 2 contain a dabsylate electrophile (BFRM 2) at the 5' end. SYBR Green I was used to monitor DNA amplification of double-stranded ACR products. In each reaction, the concentration of the nucleophilic primer was 200 nM, and the electrophilic primer was 100 nM. A 28-mer dsDNA nucleic acid template was added at 0.01 nM concentration. Reactions were thermocycled on an ABI PRISM® 7900HT Sequence Detection System, using a touchdown annealing strategy from 22° C. to 10° C., and a 95° C. melting temperature. The clipped, normalized baselined data (delta Rn, for cycles 3-8) was exported into Excel, and the plots were smoothed by a 6-point rolling average of the data. FIG. 2 illustrates specificity of the methods disclosed herein for detection of SNPs.

Example 4

ACR Detection with Unquenched Detection Group

Figure 4:
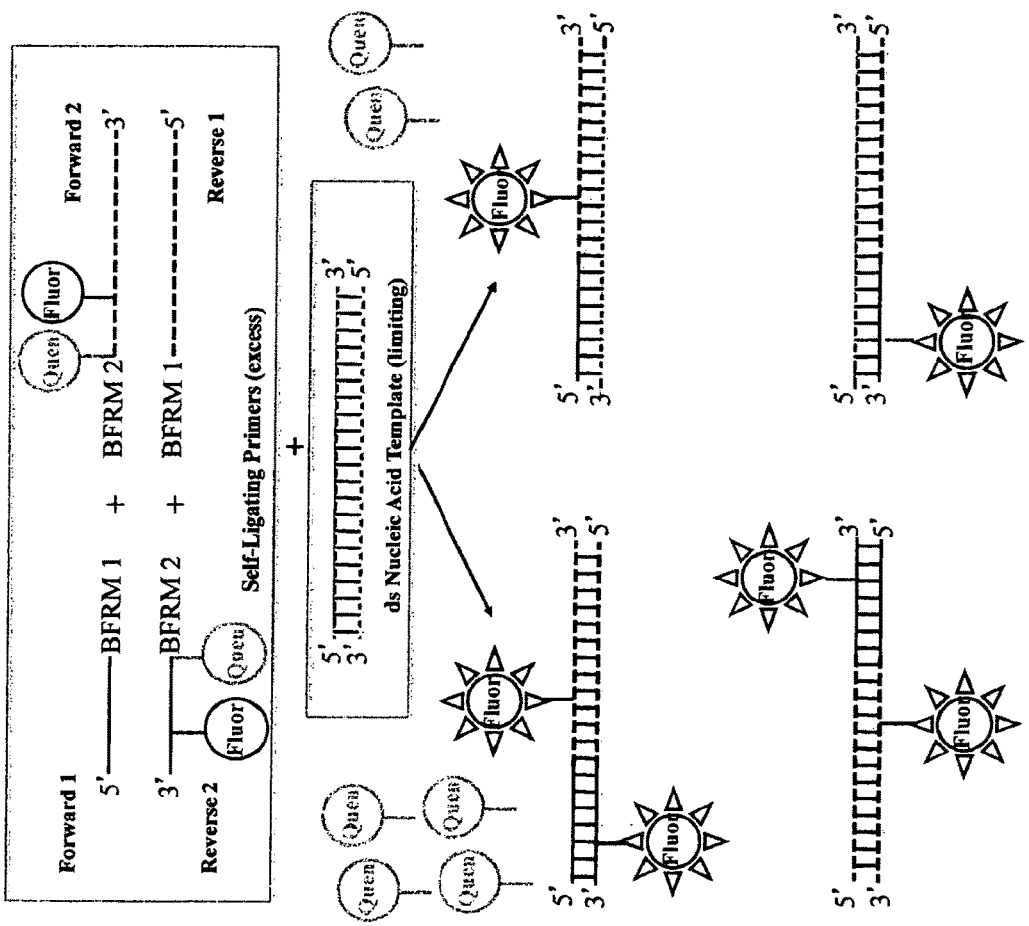
FIG. 4 illustrates the strategy and expected results from two rounds of ACR, in which four double-stranded products are generated from the amplification of a single nucleic acid target sequence, and detection with a detection group (Fluor) in which a quenching moiety (Quen) is separated from the detection group after annealing and autoligation separates the quenching moiety from the detectable group before the ligated product is detected. This illustrates that different detection groups can be used with ACR.

An example using a fluorophore/quenched detection group and expected results from two rounds of ACR, in which four double-stranded products are generated from the amplification of a single nucleic acid target sequence, and detection with a detection group (Fluor) in which a quenching moiety (Quen) is separated from the detection group after annealing and autoligation separates the quenching moiety from the detectable group before the ligated product is detected (FIG. 4). Forward 1 and Reverse 1 ACR primers both contain BFRM 1 at the 3' end. Forward 2 and Reverse 2 ACR primers both contain a quenching BFRM 2 at the 5' end, and an internal signal fluorophore (Fluor), which is quenched by BFRM 2. When an excess of ACR primers are annealed in tandem to their limiting template strands, the juxtaposition of the BFRM 1 and BFRM 2 groups causes the displacement of BFRM 2 by BFRM 1 resulting in nucleic acid-templated autoligation of the tandem ACR primers on each strand.

The resulting Forward 1/2 and Reverse 1/2 ligation products are used as templates in subsequent rounds of amplification, in which the signal increases due to more Fluor becoming un-quenched at each cycle. ACR Forward 1 and ACR Reverse 2 primers, and ACR Forward 2 and ACR Reverse 1 primers are complementary pairs, which increase the specificity of the reaction by sequestering the primers in duplexes until nucleic acid templates outcompete the formation of ACR primer homoduplexes by annealing to the primers. Because tandemly-annealed primers on a template have significantly higher melting temperatures than individual primers annealed to the same template, due to stabilizing base-pair stacking interactions between the tandemly-aligned primers, ACR can be performed at annealing temperatures that favor the formation of ACR primer/template heteroduplexes over homoduplexed primer sets. See Lane, M. J., Paner, T., Kashin, I., Faldasz, B. D., Li, B., Gallo, F. J. & Benight, A. S. (1997). The thermodynamic advantage of DNA oligonucleotide 'stacking hybridization' reactions: energetics of a DNA nick. Nucleic Acids Research, 25(3), 611-617. A variety of bond-forming reactive moieties can be used with the methods described herein, which are not limited to any specific bond-forming chemistry.

Example 5

ACR Detection with FRET Detection Groups

Figure 5:
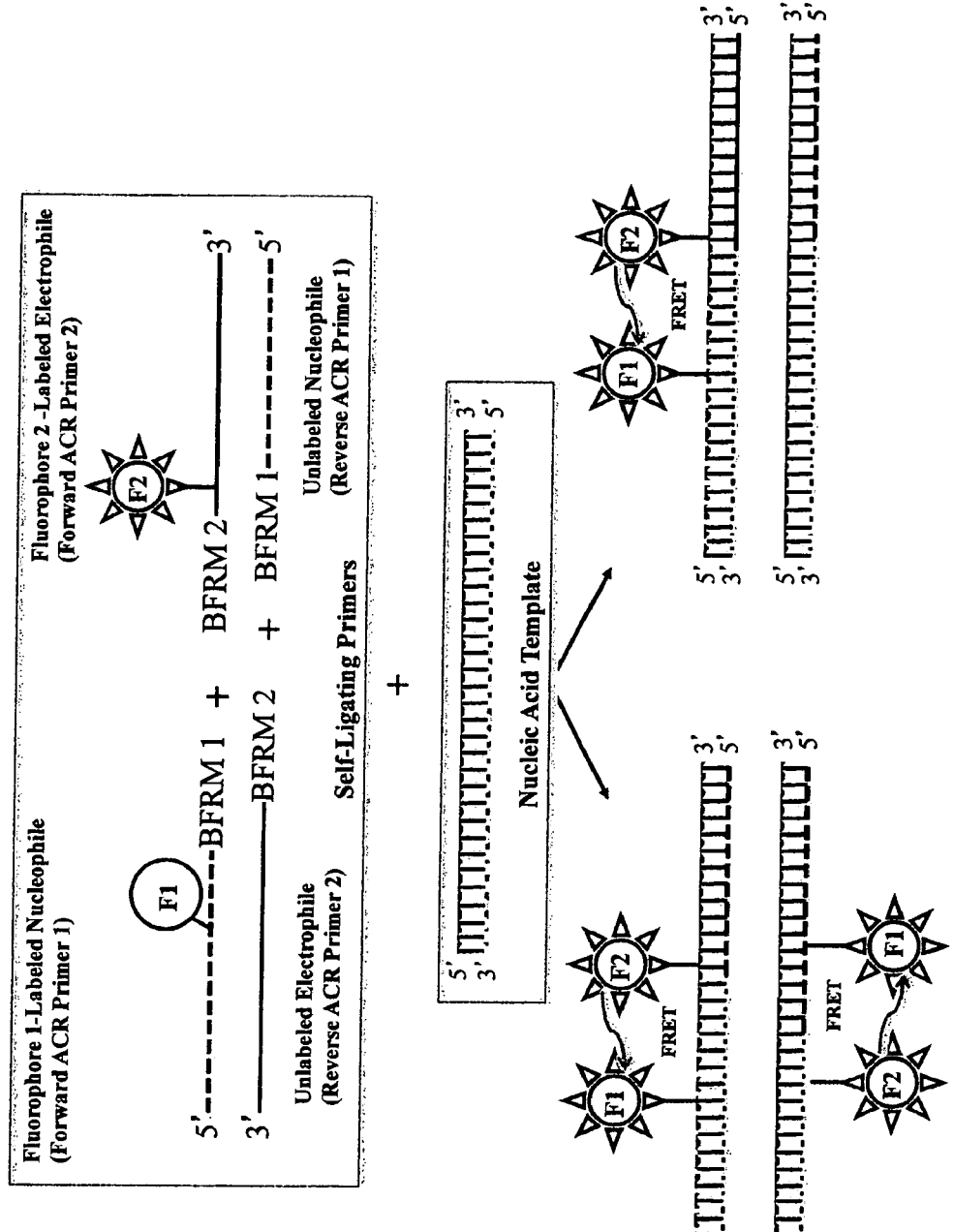
FIG. 5 illustrates the strategy and expected results from two rounds of ACR, in which four double-stranded products are generated from the amplification of a single nucleic acid target sequence, and detection with detection groups (F1 and F2) by FRET. This illustrates that different detection strategies can be used with ACR.

An example of FRET detection and expected results from two rounds of ACR, in which four double-stranded products are generated from the amplification of a single nucleic acid target sequence, and detection with a first fluorophore detection group (F1) and a second fluorophore detection group (F2) by FRET (FIG. 5). Forward ACR Primer 1 and Reverse ACR Primer 1 both contain a BFRM 1 at the 3' end. Forward ACR Primer 2 and Reverse ACR Primer 2 both contain a BFRM 2 at the 5' end. When forward and reverse primers are annealed in tandem to template, the juxtaposition of the BFRM 1 and BFRM 2 groups results in a nucleic acid-templated autoligation reaction without any enzymes or nucleotides. Primers annealed in tandem have higher melting temperature due to stabilizing base-pair stacking interactions between the tandemly-aligned oligos. See Lane, M. J., Paner, T., Kashin, I., Faldasz, B. D., Li, B., Gallo, F. J. & Benight, A. S. (1997). The thermodynamic advantage of DNA oligonucleotide 'stacking hybridization' reactions: energetics of a DNA nick. Nucleic Acids Research, 25(3), 611-617. ACR can be performed at annealing temperatures that favor the formation of primer/template heteroduplexes over primer dimers in homoduplexes. The resulting autoligation products are used as templates in subsequent rounds of exponential amplification. A variety of bond-forming reactive moieties can be used with the methods described herein, which are not limited to any specific bond-forming chemistry.

Example 6

ACR Detection with Stained Polyacrylamide Gels

Figure 6:
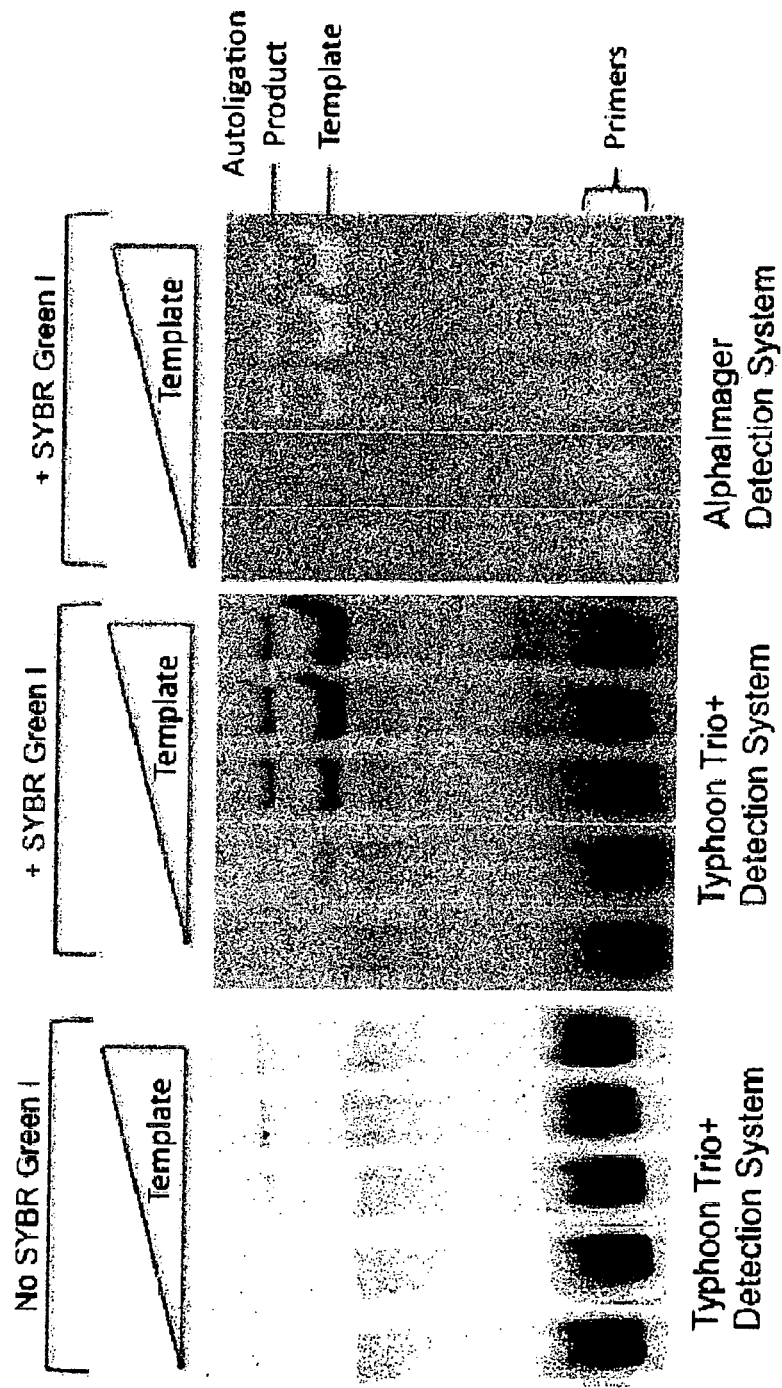
FIG. 6 shows unstained and stained polyacrylamide gels after an autoligation reaction with a first forward primer nucleic acid containing a first bond-forming reactive moiety and a second forward primer nucleic acid containing a second bond-forming reactive moiety in which the second forward primer is labeled with FAM, thus illustrating that different detection media and different detection platforms can be used with ACR.

An example of results of ACR self-ligation reactions using unstained and stained polyacrylamide gels after an autoligation reaction for detection where the first forward primer nucleic acid contains a first bond-forming reactive moiety and a second forward primer nucleic acid contains a second bond-forming reactive moiety in which the second forward primer is labeled with FAM (FIG. 6). Reactions were performed using unlabeled Forward ACR Primer 1 nucleophile (GCAACGACCGTTCCGT-SH) (SEQ ID NO: 1) and labeled Forward ACR Primer 2 electrophile (BrAc-TCAAT(FAM)ACTGCGCAGCC) (SEQ ID NO: 2). Increasing ssDNA nucleic acid template was added to reactions in a molar excess. FIG. 6 shows the efficiency of the forward ACR primers for autoligation by titrating in increasing amounts of single-stranded complementary nucleic acid template. Lane 1 of each panel is the no-template control. The three panels show the same gel using different detection systems. The left panel shows FAM fluorescence using the Typhoon Trio+ imaging system. The middle panel shows SYBR fluorescence using the Typhoon Trio+ imaging system after staining the gel with SYBR Green I. The right panel shows SYBR fluorescence using the AlphaImager imaging system after staining the gel with SYBR Green I. Different detection media and different detection platforms can be used with the methods herein, which are not limited to a single detection medium or detection platform.

Example 7

Unlabeled ACR Primer Detection with Stained Polyacrylamide Gels

Figure 7:
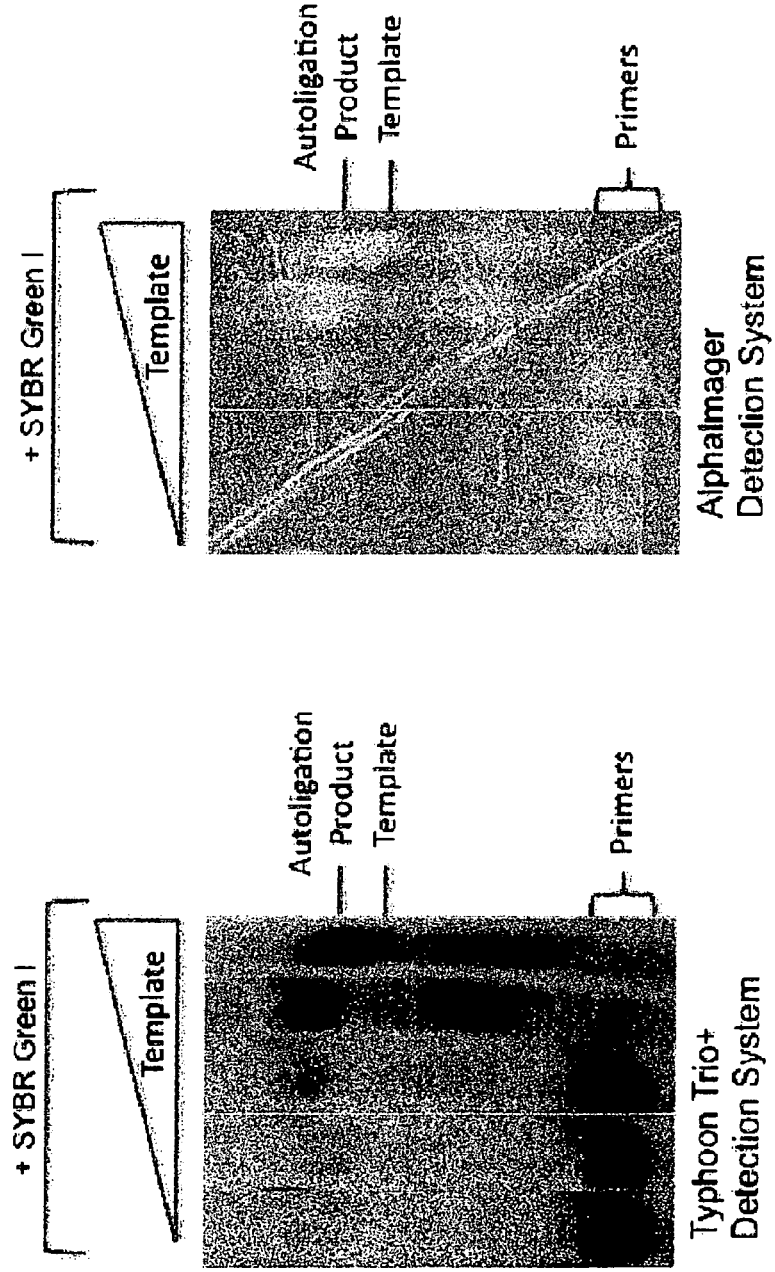
FIG. 7 shows a stained polyacrylamide gel after an autoligation reaction with a first reverse primer nucleic acid containing a first bond-forming reactive moiety and a second reverse primer nucleic acid containing a second bond-forming reactive moiety in which the first and second reverse primers are unlabeled.

An example of results of ACR self-ligation reactions using a stained polyacrylamide gel after an autoligation reaction with a first reverse primer nucleic acid containing a first bond-forming reactive moiety and a second reverse primer nucleic acid containing a second bond-forming reactive moiety in which the first and second reverse primers are unlabeled. Reactions were performed using unlabeled Reverse ACR Primer 1 nucleophile (GGCTGCGCAGTAT-SH) (SEQ ID NO: 3) and unlabeled Reverse ACR Primer 2 electrophile (BrAc-TGAACGGAACGGTCGTTGC) (SEQ ID NO: 4). Increasing ssDNA nucleic acid template was added to reactions in a molar excess (lanes 2-5). Lane 1 of each panel is the no-template control. FIG. 7 shows 2 panels of the same gel using different detection systems. The left panel shows SYBR fluorescence using the Typhoon Trio+ imaging system after staining the gel with SYBR Green I. The right panel shows SYBR fluorescence using the AlphaImager imaging system after staining the gel with SYBR Green I.

Example 8

ACR Primer FRET Detection with Unstained Polyacrylamide Gels

Figure 8:
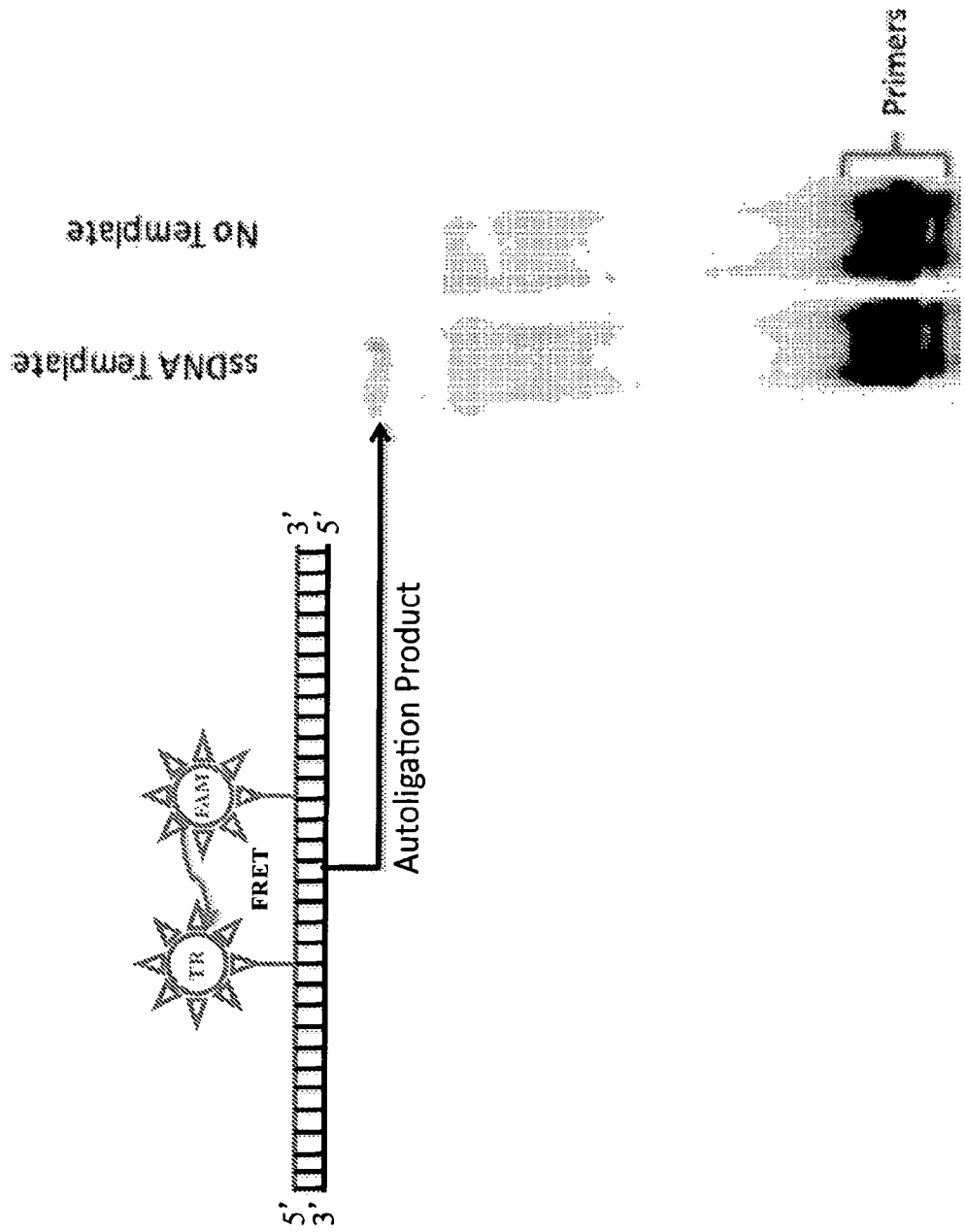
FIG. 8 shows FAM/Texas Red FRET fluorescence of ACR reactions on an unstained 20% acrylamide+urea denaturing gel using the Typhoon Trio+ imaging system.

An example of results of ACR showing FAM/Texas Red FRET fluorescence of ACR reactions on an unstained (FIG. 8). Reactions were performed using Texas Red-labeled Forward ACR Primer 1, FAM-labeled Forward ACR Primer 2, and unlabeled reverse primers, with ssDNA nucleic acid as template. FIG. 8 shows FAM/Texas Red FRET fluorescence of reactions on an unstained 20% acrylamide+urea denaturing gel using the Typhoon Trio+ imaging system. Lane 1 contains ssDNA template, and Lane 2 is the no-template control. The autoligation product was excited at 488 nM and the fluorescence emission was detected at both 520 nM (FAM channel) and 610 nM (Texas Red FRET channel) on the Typhoon Trio+ imaging system, demonstrating FRET detection after thermocycling.

Example 9

ACR Activity Enrichment

Figure 9:
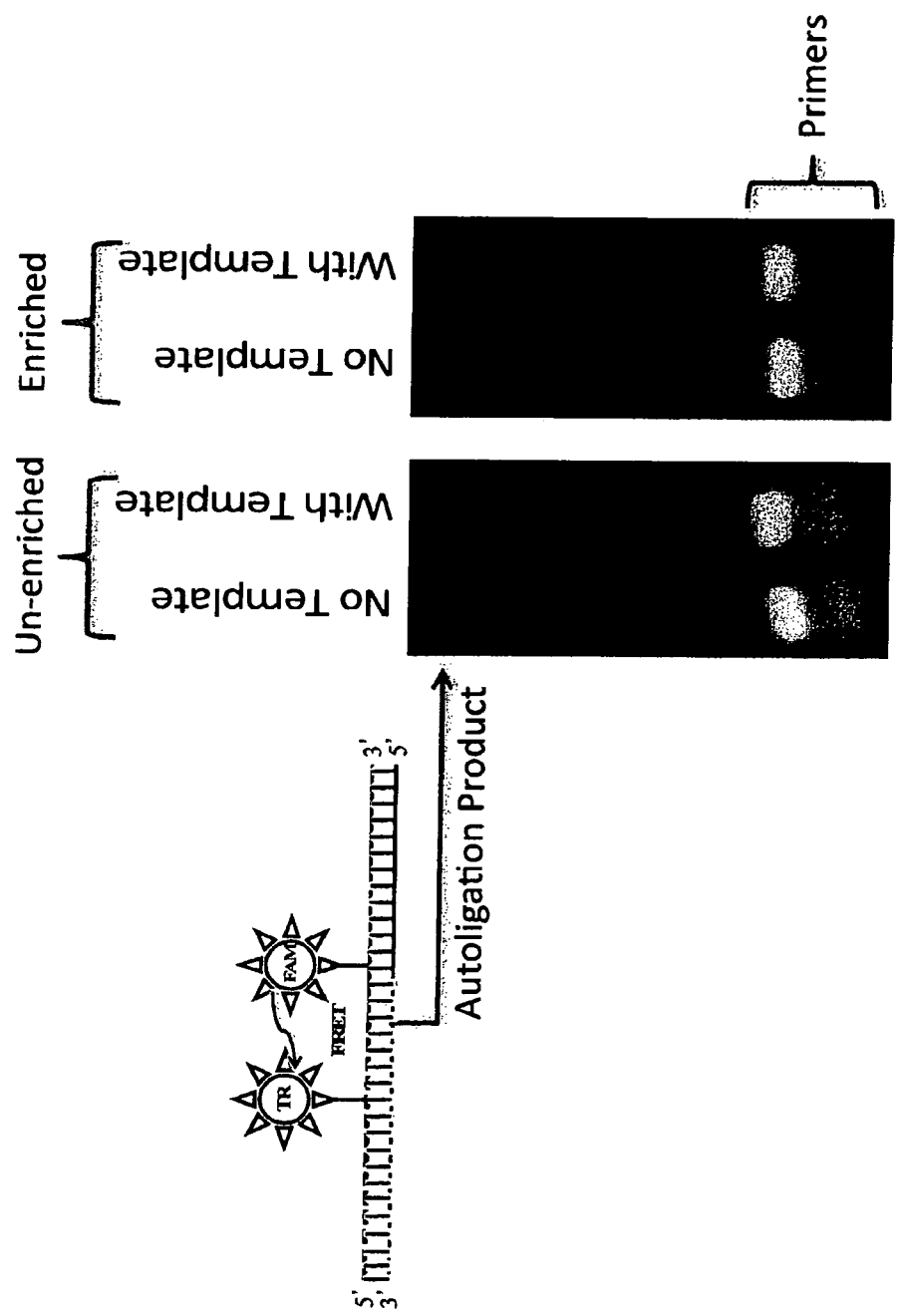
FIG. 9 shows enrichment of ACR activity using different fractions electrophilic ACR primers. Detection used FAM/Texas Red FRET fluorescence of ACR reactions on an unstained 20% acrylamide+urea denaturing gel using the Typhoon Trio+ imaging system.

An example of results showing enrichment of ACR activity using different fractions of electrophilic ACR primers (FIG. 9). Detection used FAM/Texas Red FRET fluorescence of ACR reactions on an unstained 20% acrylamide+urea denaturing gel using the Typhoon Trio+ imaging system. FIG. 9 shows FAM/Texas Red FRET fluorescence of reactions on an unstained 20% acrylamide+urea denaturing gel using the Typhoon Trio+ detection system. Reactions were performed using Texas Red-labeled Forward ACR Primer 1 and FAM-labeled Forward ACR Primer 2 with ssDNA nucleic acid as template. Lanes 1 and 3 are the no-template control lanes. Lanes 2 and 4 contain ssDNA template. The autoligation reactions were excited at 488 nM and the fluorescence emission was detected at both 520 nM (FAM channel) and 610 nM (Texas Red FRET channel) on the Typhoon Trio+ detection system, demonstrating FRET detection.

Example 10

ACR FRET Enhancement

Figure 10:
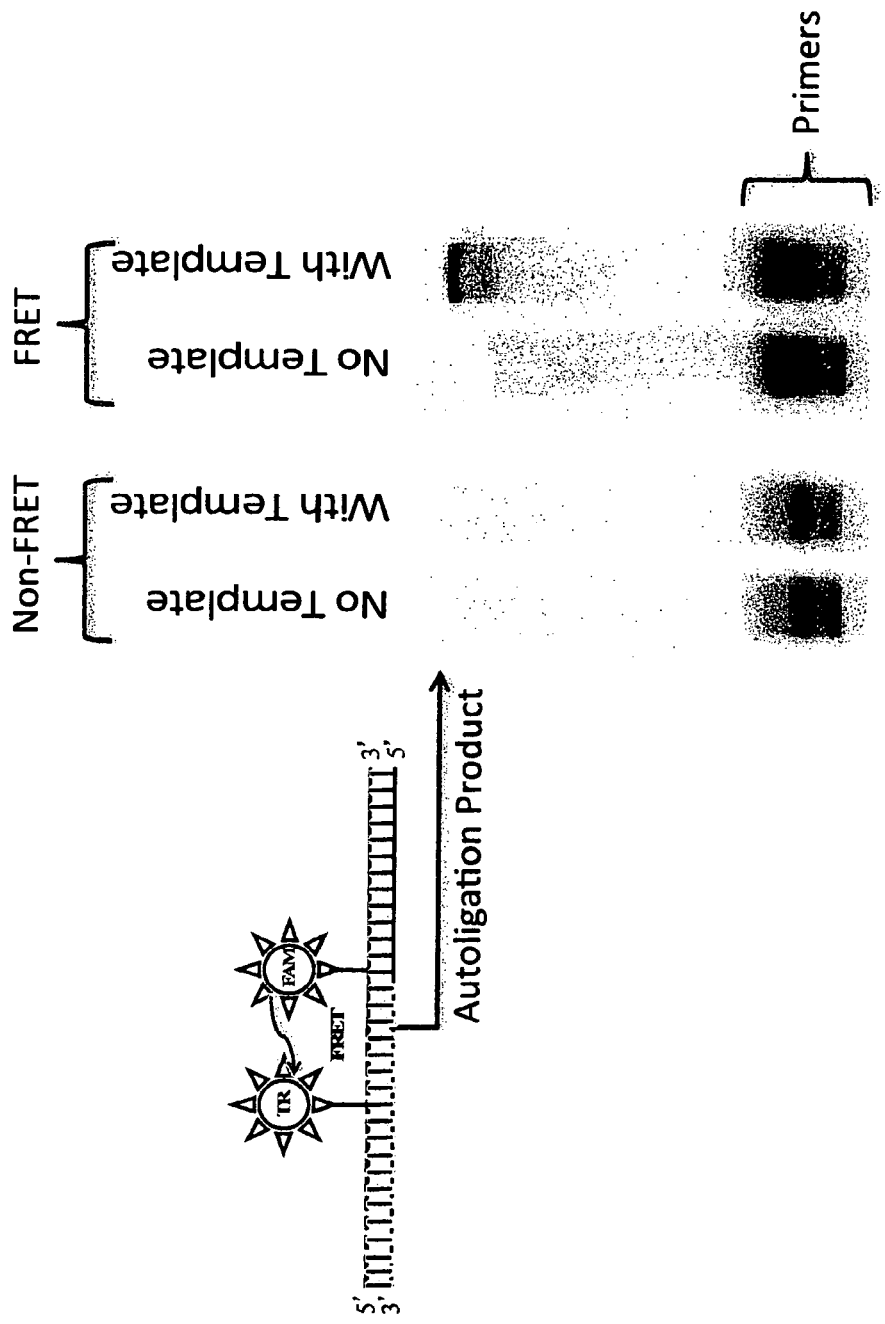
FIG. 10 shows enhancement of FRET using the same reactions with enriched ACR activity from FIG. 9 (Lanes 3 and 4) using two different channels for detection: Non-FRET and FRET channels.

An example of results showing enhancement of ACR FRET using the same reactions with enriched ACR activity from FIG. 9 (Lanes 3 and 4) using two different channels for detection: Non-FRET and FRET channels (FIG. 10). Detection used FAM/Texas Red FRET fluorescence of ACR reactions on an unstained 20% acrylamide+urea denaturing gel using the Typhoon Trio+ imaging system. Reactions were performed using Texas Red-labeled Forward ACR Primer 1 and FAM-labeled Forward ACR Primer 2 with ssDNA nucleic acid as template. Lanes 1 and 3 are the no-template control lanes. Lanes 2 and 4 contain ssDNA template. The reactions were excited at 488 nM and the fluorescence emission was detected at 520 nM (FAM channel) (Lanes 1 and 2) and at 610 nM (Texas Red FRET channel) (Lanes 3 and 4) on the Typhoon Trio+ detection system, demonstrating FRET detection.

Examples 11A and 11B

ACR Real-Time FRET Detection

Figure 11A:
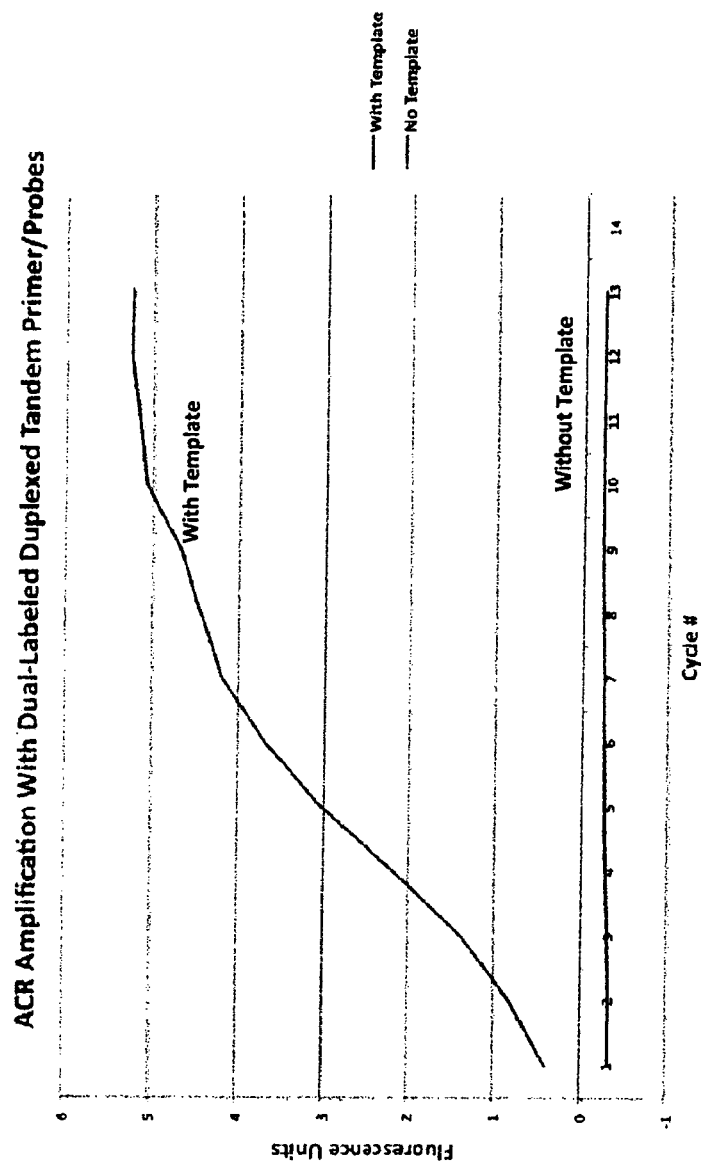
FIG. 11A shows real-time amplification plots on a Light-Cycler® 480 II instrument using FAM/Texas Red FRET fluorescence in ACR reactions to demonstrate exponential amplification.
Figure 11B:
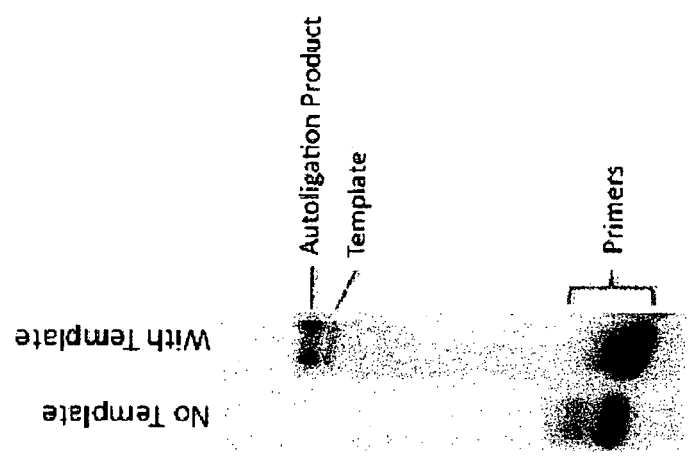
FIG. 11B shows the same reaction products run on a SYBR Green I stained 20% acrylamide+urea denaturing gel using the Typhoon Trio+ imaging system. This illustrates that ACR can be detected in real-time, and therefore ACR can be used for both end-point and quantitative analyses.

An example of results showing real-time amplification plots on the LightCycler® 480 II using FAM/Texas Red FRET fluorescence in ACR reactions to demonstrate exponential amplification (FIG. 11A). Reactions were performed using Texas Red-labeled Forward ACR Primer 1, FAM-labeled Forward ACR Primer 2, and unlabeled reverse primers, with ssDNA nucleic acid as template. The normalized baselined data was exported into Excel, and the plots were smoothed by a 4-point rolling average of the data. The trace plot labeled "With Template" shows exponential amplification of a reaction with template, DNA, and the "No Template" plot shows a negative no-template control. The same reactions were run on a SYBR Green I stained 20% acrylamide+urea denaturing gel using the Typhoon Trio+ imaging system (FIG. 11 B). Lane 1 contains the no-template control, while Lane 2 shows the amplification product in the presence of template. This illustrates that ACR can be detected in real-time, and therefore ACR can be used for both end-point and quantitative analyses.

Example 12

ACR Bond-Forming Chemistry Through Cycloaddition

A non-limiting example of an ACR bond-forming chemistry through cycloaddition with alkyne and azide moieties to generate a covalent carbon-heteroatom bond between species to form a 1,2,3-triazole conjugate (FIG. 12). The cycloaddition chemistry reaction couples and azide group with an alkyne group through a copper-catalyzed (Cu(I)) reaction. The reaction is stable, irreversible, and has no side products, and the bond-forming alkyne and azide moieties are commercially available. See Rostovtsev, V. V., et al. (2002). A stepwise huisgen cycloaddition process: copper (I)-catalyzed regioselective "ligation" of azides and terminal alkynes. Angew Chem Int Ed Engl. 41(14): 2596-2599; Moses, J. E. and A. D. Moorhouse, (2007). The growing applications of click chemistry. Chem Soc Rev. 36(8): 1249-1262.

Example 13

ACR Bond-Forming Reactive Moiety with Hexynyl

A non-limiting example of a bond-forming reactive moiety using a hexynyl alkyne modification (FIG. 13). Hexynyl can be used to conjugate an ACR Primer 2 to an ACR Primer 1 modified with an azide bond-forming reactive moiety.

Example 14

ACR Bond-Forming Reactive Moiety with Octadiynyl

A non-limiting example of a bond-forming reactive moiety using a hexynyl an octadiynyl alkyne modification (FIG. 14). Octadiynyl can be used to conjugate an ACR Primer 2 to an ACR Primer 1 modified with an azide bond-forming reactive moiety.

Example 15

ACR Primers Containing Azide and Alkyne Bond-Forming Reactive Moieties

Non-limiting examples showing ACR primer sequences containing an azide bond-forming reactive moiety (3AzideN, Integrated DNA Technologies), and hexynyl (5Hexynyl, Integrated DNA Technologies) and octadiynyl (55 OCTdU, Integrated DNA Technologies) alkyne bond-forming reactive moieties to detect a mutation 18-599m in the maize Glutathione S-Transferase (GST) gene (FIG. 15). See Rostovtsev, V. V., et al. (2002). A stepwise huisgen cycloaddition process: copper(I)-catalyzed regioselective "ligation" of azides and terminal alkynes. Angew Chem Int Ed Engl. 41(14): 2596-2599; Moses, J. E. and A. D. Moorhouse, (2007). The growing applications of click chemistry. Chem Soc Rev. 36(8): 1249-1262.

Detection is performed through FRET using a fluorescein (iFluorT) and TAMRA (i6-TAMN) detection groups.

Examples 16A and 16B

ACR with Azide and Hexynyl Bond-Forming Reactive Moieties

Figure 16A:
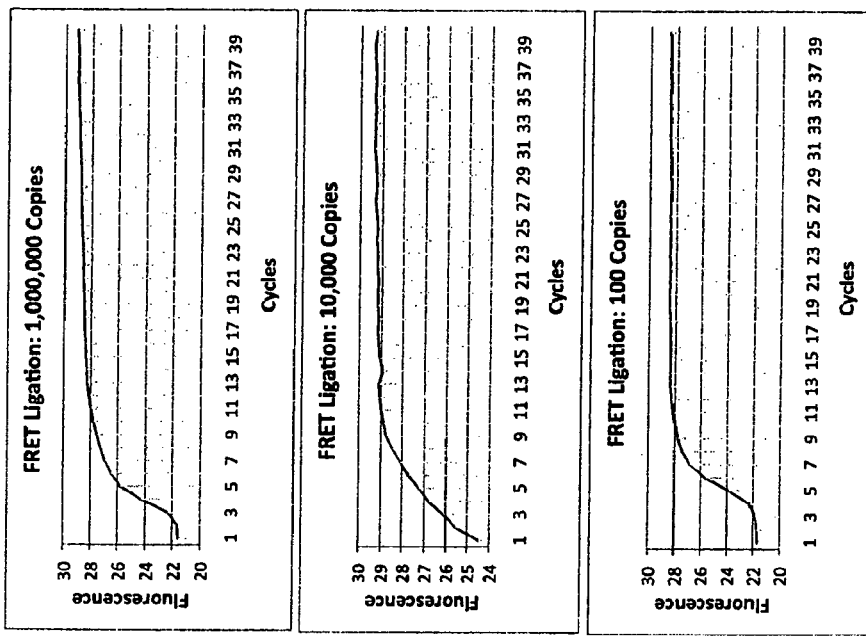
FIG. 16A shows real-time amplification plots of ACR with azide and hexynyl bond-forming reactive moieties detected on the LightCycler® 480 II using FAM/TAMRA FRET fluorescence in ACR reactions to demonstrate exponential amplification down to 100 copies of template.
Figure 16B:
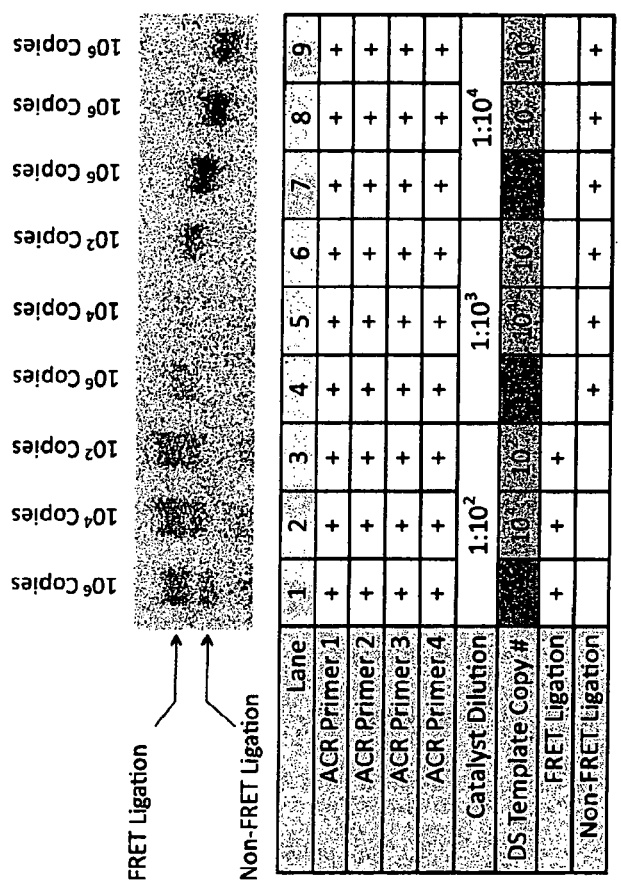
FIG. 16B shows FRET ligation fluorescence of the same reaction products in lanes 1-3 run on a 20% acrylamide+urea denaturing gel using the Typhoon Trio+ imaging system. FRET ligation is not observed with lower concentrations of the catalyst (lanes 4-9). This illustrates that azide and hexynyl bond-forming reactive moieties have greater sensitivity with an enhanced exponential amplification profile over thiol nucleophilic and bromoacetate electrophilic moieties in ACR (FIGS. 11A and 11B), making ACR more amenable to both end-point and quantitative analyses.
Figure 17:
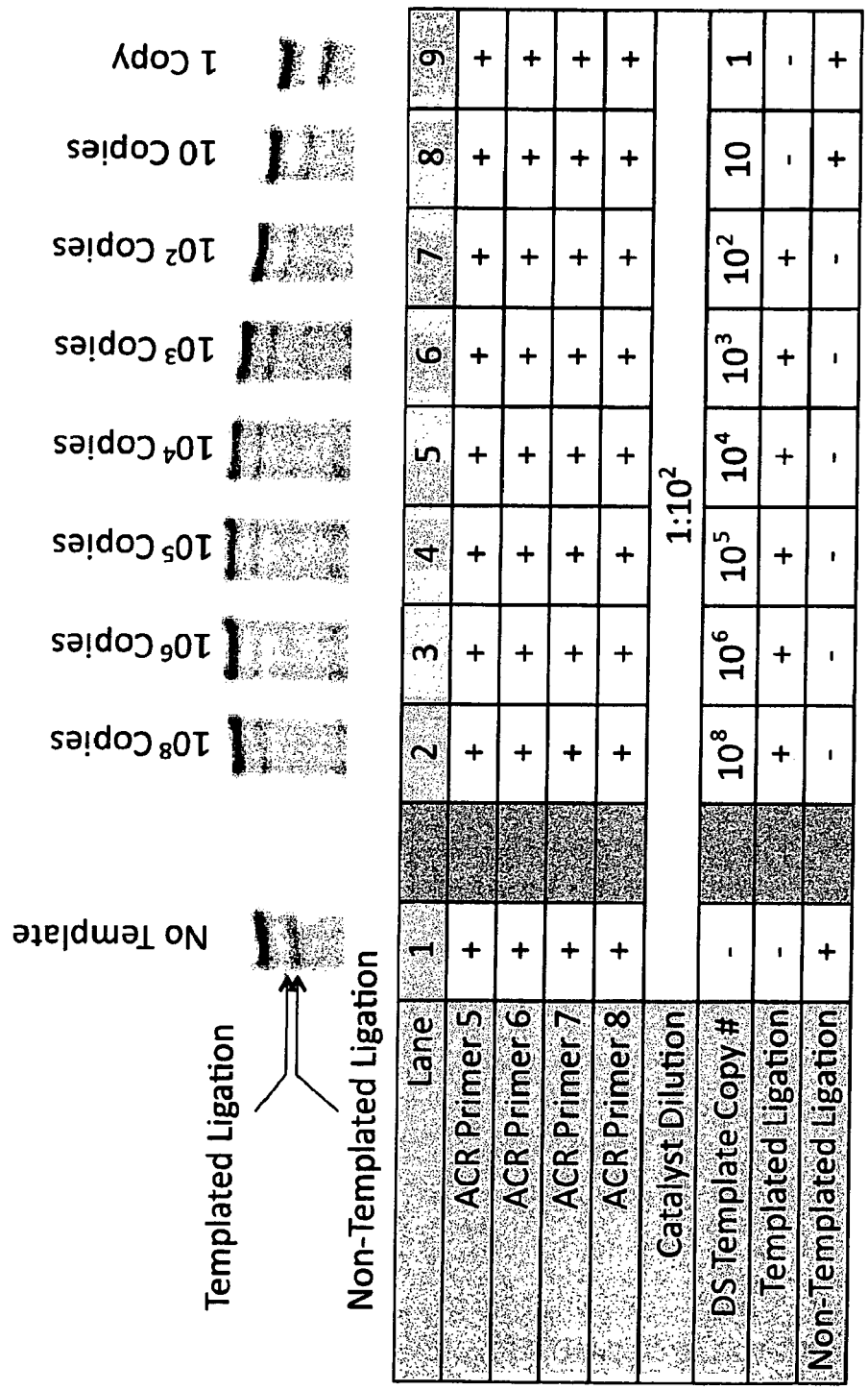
FIG. 17 shows templated ligation of ACR reactions using azide and octadiynyl bond-forming reactive moieties run on a 20% acrylamide+urea denaturing gel using the Typhoon Trio+ imaging system. FRET templated ligation is observed down to 100 copies of template (lanes 2-7). This illustrates that azide and octadiynyl bond-forming reactive moieties have greater sensitivity over thiol nucleophilic and bromoacetate electrophilic moieties in ACR (FIGS. 11A and 11B), making ACR more amenable to both end-point and quantitative analyses.
Figure 18:
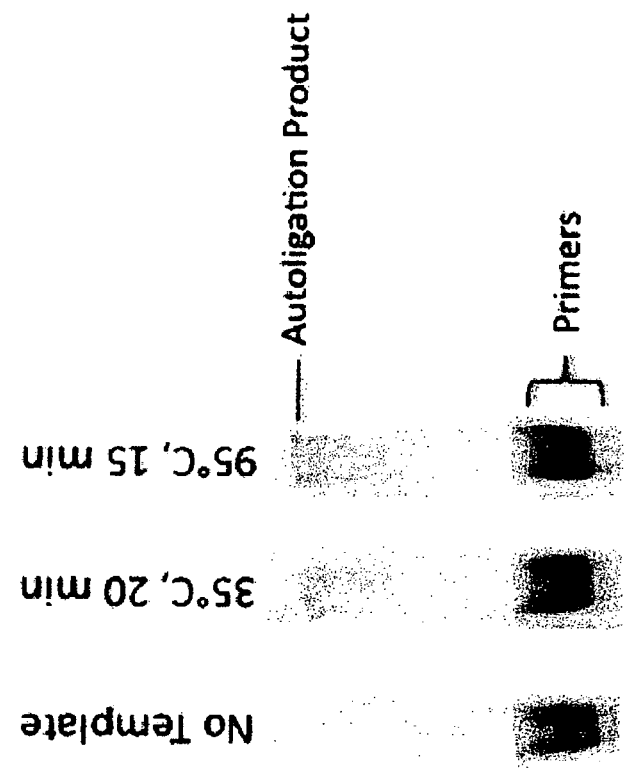
FIG. 18 shows thermal stability of bond-forming reactive moieties on first and second forward primer nucleic acids in which the second forward primer nucleic acid contains FAM and FAM fluorescence of the autoligation reaction is detected on an unstained 20% acrylamide+urea denaturing gel using the Typhoon Trio+ imaging system.
Figure 19:
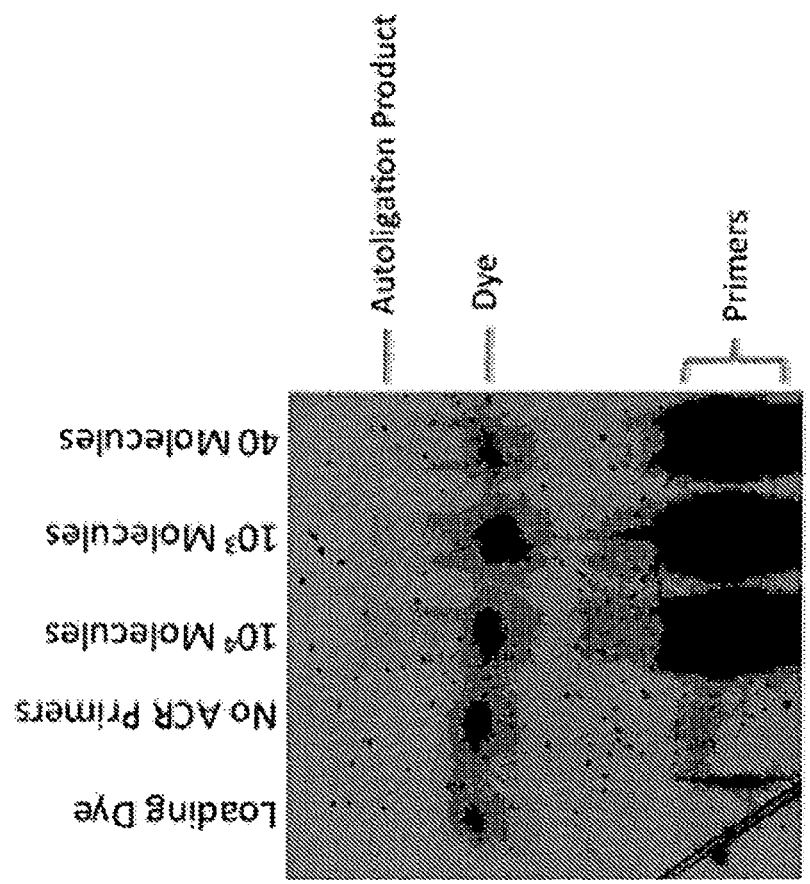
FIG. 19 shows FAM/Texas Red FRET fluorescence in ACR reactions with decreasing amounts of template on an unstained 20% acrylamide+urea denaturing gel using the Typhoon Trio+ imaging system.

An example of results showing real-time amplification plots with cycloaddition on the LightCycler® 480 II using FAM/TAMRA FRET fluorescence in ACR reactions to demonstrate exponential amplification (FIG. 16A). Reactions were performed using FAM-labeled Forward ACR Primer 1, TAMRA-labeled Forward ACR Primer 2, and unlabeled reverse primers, with dsDNA nucleic acid as template. The non-baselined data were exported into Excel. The trace plots show enhanced exponential amplification profiles over thiol nucleophilic and bromoacetate electrophilic moieties in ACR (FIGS. 11A and 11B), making ACR more amenable to both end-point and quantitative analyses. The same reactions were run on a 20% acrylamide+urea denaturing gel using the Typhoon Trio+ imaging system (FIG. 16 B). Lanes 1-3 contain more concentrated catalyst than lanes 4-9 and show FRET-specific fluorescence of the ligated ACR primers. This illustrates that azide and hexynyl bond-forming reactive moieties have greater sensitivity with an enhanced exponential amplification profile over thiol nucleophilic and bromoacetate electrophilic moieties in ACR (FIGS. 11A and 11B), making ACR more amenable to both end-point and quantitative analyses.

Example 17

ACR with Azide and Octadiynyl Bond-Forming Reactive Moieties

An example of results showing real-time amplification using azide and octadiynyl bond-forming reactive moieties with FAM/TAMRA FRET fluorescence in ACR run on a 20% acrylamide+urea denaturing gel using the Typhoon Trio+ imaging system. FRET templated ligation is observed down to 100 copies of template (lanes 2-7). This illustrates that azide and octadiynyl bond-forming reactive moieties have greater sensitivity over thiol nucleophilic and bromoacetate electrophilic moieties in ACR (FIGS. 11A and 11B), making ACR more amenable to both end-point and quantitative analyses.

Example 18

Thermostability of ACR Primers

Reactions were performed using unlabeled Forward ACR Primer 1 and FAM-labeled Forward ACR Primer 2. ssDNA oligo template was added to the reactions at a 33-fold molar excess. Reactions were set up at room temperature and incubated at 35° C. for 20 min., and then thermocycled in a MultiGene Labnet thermocycler. The thermocycling protocol was 95° C. for 5 min., then 40 cycles of 95° C., 30 sec. and 20° C., 1 min. The reactions were stopped with equal volumes of formamide containing dye, heat denatured, cooled on ice, and load directly onto the denaturing gel. FIG. 20 shows FAM fluorescence of reactions on an unstained 20% acrylamide+urea denaturing gel using the Typhoon Trio+ imaging system. Lane 1 is the no-template control. Lane 2 contains primers pre-heated at 35° C. for 20 min. Lane 3 contains primers pre-heated at 95° C. for 15 min. ACR primers pretreated for 15 min. at 95° C. show similar reactivity to primers pretreated for 20 min. at 35° C., prior to thermocycling. Also, no decrease in autoligation reactivity was also observed when 95° C.-treated ACR primers were compared to primers incubated at room temperature (data not shown).

Example 19

Determination of Limit of Detection

Reactions were performed using Texas Red-labeled Forward ACR Primer 1, FAM-labeled Forward ACR Primer 2, and unlabeled reverse primers, with a titration of dsDNA oligo template. The reactions were stopped with equal volumes of formamide containing dye, heat denatured, cooled on ice, and load directly onto the denaturing gel. FIG. 10 shows FAM/Texas Red FRET fluorescence of reactions on an unstained 20% acrylamide+urea denaturing gel using the Typhoon Trio+ imaging system with excitation channel 488 nm and emission channel 610 nm. Lane 3 is from 10,000 molecules, Lane 4 is from 1,000 molecules, and lane 5 is from 40 molecules of template. The band in the middle of the gel is observed in both the loading dye lane (Lane 1) and the lane with only template (Lane 2). Autoligation products are visible from reactions containing 10,000 and 1,000 molecules, but not from the reaction containing 40 molecules. The autoligation product is also not observed without template (data not shown). These results demonstrate the feasibility of exponential amplification using ACR primers.

The invention claimed is:

1. A reagent composition for amplifying a target nucleic acid sequence comprising:
   a first forward oligonucleotide having a first bond-forming reactive moiety;
   a second forward oligonucleotide having a second bond-forming reactive moiety;
   a first reverse oligonucleotide having a third bond-forming reactive moiety; and
   a second reverse oligonucleotide having a fourth bond-forming reactive moiety;
   wherein the first forward oligonucleotide, the second forward oligonucleotide, the first reverse oligonucleotide, or the second reverse oligonucleotide is configured to specifically anneal with the target nucleic acid sequence; and wherein
   the first forward oligonucleotide comprises the first bond-forming reactive moiety that is an azide group conjugated to a 3' terminus of the first forward oligonucleotide, and the second forward oligonucleotide comprises the second bond-forming reactive moiety that is an alkyne group conjugated to a 5' terminus of the second forward oligonucleotide; or the first forward oligonucleotide comprises the first bond-forming reactive moiety that is an alkyne group conjugated to a 3' terminus of the first forward oligonucleotide, and the second forward oligonucleotide comprises the second bond-forming reactive moiety that is an azide group conjugated to a 5' terminus of the second forward oligonucleotide;
   the first reverse oligonucleotide comprises the third bond-forming reactive moiety that is an azide group conjugated to a 3' terminus of the first reverse oligonucleotide, and the second reverse oligonucleotide comprises the fourth bond-forming reactive moiety that is an alkyne group conjugated to a 5' terminus of the second reverse oligonucleotide; or the first reverse oligonucleotide comprises the third bond-forming reactive moiety that is an alkyne group conjugated to a 3' terminus of the first reverse oligonucleotide, and the second reverse oligonucleotide comprises the fourth bond-forming reactive moiety that is an azide group conjugated to a 5' terminus of the second reverse oligonucleotide;
   the first forward oligonucleotide and the second forward oligonucleotide are fully complementary to the target nucleic acid sequence and the first bond-forming reactive moiety and the second bond-forming reactive moiety are juxtaposed when annealed to the target nucleic acid sequence; and
   the first reverse oligonucleotide and the second reverse oligonucleotide are fully complementary to a complement of the target nucleic acid sequence and the third bond-forming reactive moiety and the fourth bond-forming reactive moiety are juxtaposed when annealed to the complement of the target nucleic acid sequence.

2. The reagent composition of claim 1, wherein the first bond-forming reactive moiety or the third bond-forming reactive moiety is an azide, and the second bond-forming reactive moiety or the fourth bond-forming reactive moiety is an alkyne.

3. The reagent composition of claim 1, wherein the first bond-forming reactive moiety or the third bond-forming reactive moiety is an alkyne, and the second bond-forming reactive moiety or the fourth bond-forming reactive moiety is an azide.

4. The reagent composition of claim 2, wherein the alkyne is cycloctyne.

5. The reagent composition of claim 1, wherein the first bond-forming reactive moiety and the second bond-forming reactive moiety are configured to form a chemical bond in an absence of an enzyme when juxtaposed on the target nucleic acid sequence.

6. The reagent composition of claim 1, wherein the third bond-forming reactive moiety and the fourth bond-forming reactive moiety are configured to form a chemical bond in an absence of an enzyme when juxtaposed on the target nucleic acid sequence.

7. The reagent composition of claim 1, wherein at least one of the first forward oligonucleotide, the second forward oligonucleotide, the first reverse oligonucleotide, or the second reverse oligonucleotide is conjugated to a detectable group.

8. The reagent composition of claim 1, wherein the first forward oligonucleotide or the first reverse oligonucleotide comprises a FRET donor fluorophore and the second forward oligonucleotide or the second or reverse oligonucleotide comprises a FRET acceptor fluorophore.

9. The reagent composition of claim 1, wherein the first forward oligonucleotide or the first reverse oligonucleotide comprises a FRET acceptor fluorophore and the second forward oligonucleotide or the second reverse oligonucleotide comprises a FRET donor fluorophore.

10. The reagent composition of claim 1, wherein the first forward oligonucleotide or the first reverse oligonucleotide comprises a quenched dye or detectable group and the second forward oligonucleotide or the second reverse oligonucleotide comprises a quenching moiety.

11. The reagent composition of claim 1, wherein the first forward oligonucleotide or the first reverse oligonucleotide comprises a quenching moiety and the second forward oligonucleotide or the second reverse oligonucleotide comprises a quenched dye or detectable group.

12. The reagent composition of claim 1, further comprising a double-stranded nucleic acid binding dye.

13. The reagent composition of claim 1, wherein each of the first forward oligonucleotide, the second forward oligonucleotide, the first reverse oligonucleotide, and the second reverse oligonucleotide is from 5 to 35 nucleotides in length.

14. The reagent composition of claim 1, further comprising a buffer.

15. The reagent composition of claim 1, further comprising a salt.

16. The reagent composition of claim 1, wherein the reagent composition does not comprise an enzyme.

17. The reagent composition of claim 1, wherein the reagent composition does not comprise a nucleotide.

18. A kit for amplifying two or more target nucleic acid sequences, comprising:
  a first forward oligonucleotide having a first bond-forming reactive moiety;
  a second forward oligonucleotide having a second bond-forming reactive moiety;
  a first reverse oligonucleotide having a third bond-forming reactive moiety; and
  a second reverse oligonucleotide having a fourth bond-forming reactive moiety;
  wherein the first forward oligonucleotide, the second forward oligonucleotide, the first reverse oligonucleotide, or the second reverse oligonucleotide is configured to specifically anneal with a target nucleic acid sequence; and wherein
  the first forward oligonucleotide comprises the first bond-forming reactive moiety that is an azide group conjugated to a 3' terminus of the first forward oligonucleotide, and the second forward oligonucleotide comprises the second bond-forming reactive moiety that is an alkyne group conjugated to a 5' terminus of the second forward oligonucleotide; or the first forward oligonucleotide comprises the first bond-forming reactive moiety that is an alkyne group conjugated to a 3' terminus of the first forward oligonucleotide, and the second forward oligonucleotide comprises the second bond-forming reactive moiety that is an azide group conjugated to a 5' terminus of the second forward oligonucleotide;
  the first reverse oligonucleotide comprises the third bond-forming reactive moiety that is an azide group conjugated to a 3' terminus of the first reverse oligonucleotide, and the second reverse oligonucleotide comprises the fourth bond-forming reactive moiety that is an alkyne group conjugated to a 5' terminus of the second reverse oligonucleotide; or the first reverse oligonucleotide comprises the third bond-forming reactive moiety that is an alkyne group conjugated to a 3' terminus of the first reverse oligonucleotide, and the second reverse oligonucleotide comprises the fourth bond-forming reactive moiety that is an azide group conjugated to a 5' terminus of the second reverse oligonucleotide;
  the first forward oligonucleotide and the second forward oligonucleotide are fully complementary to the target nucleic acid sequence and the first bond-forming reactive moiety and the second bond-forming reactive moiety are juxtaposed when annealed to the target nucleic acid sequence; and
  the first reverse oligonucleotide and the second reverse oligonucleotide are fully complementary to a complement of the target nucleic acid sequence and the third bond-forming reactive moiety and the fourth bond-forming reactive moiety are juxtaposed when annealed to the complement of the target nucleic acid sequence.

19. The kit of claim 18, wherein the two or more target nucleic acid sequences comprise a first target nucleic acid sequence and a second target nucleic acid sequence such that the second target nucleic acid sequence differs from the first target nucleic acid sequence by at least a single nucleotide or a nucleotide base pair.

20. The kit of claim 19, wherein the second target nucleic acid sequence differs from the first target nucleic acid sequence by the single nucleotide or the nucleotide base pair.

21. The kit of claim 18, further including a reagent that disrupts a DNA duplex.

22. The kit of claim 21, wherein the reagent is an organic solvent, a high pH solution, a cross-linking reagent, a chaotropic agent, a disulfide bond reducer, an oligo wedge, or a low salt concentration solution.

23. The kit of claim 18, wherein the first bond-forming reactive moiety or the third bond-forming reactive moiety is an azide, and the second bond-forming reactive moiety or the fourth bond-forming reactive moiety is an alkyne.

24. The kit of claim 18, wherein the first bond-forming reactive moiety or the third bond-forming reactive moiety is an alkyne, and the second bond-forming reactive moiety or the fourth bond-forming reactive moiety is an azide.

25. The kit of claim 23, wherein the alkyne is cycloctyne.

26. The kit of claim 18, wherein the first bond-forming reactive moiety and the second bond-forming reactive moiety are configured to form a chemical bond in an absence of an enzyme when juxtaposed on the target nucleic acid sequence.

27. The kit of claim 18, wherein the third bond-forming reactive moiety and the fourth bond-forming reactive moiety are configured to form a chemical bond in an absence of an enzyme when juxtaposed on the target nucleic acid sequence.

28. The kit of claim 18, wherein at least one of the first forward oligonucleotide, the second forward oligonucleotide, the first reverse oligonucleotide, or the second reverse oligonucleotide is conjugated to a detectable group.

29. The kit of claim 18, wherein the first forward oligonucleotide or the first reverse oligonucleotide comprises a FRET donor fluorophore and the second forward oligonucleotide or the second reverse oligonucleotide comprises a FRET acceptor fluorophore.

30. The kit of claim 18, wherein the first forward oligonucleotide or the first reverse oligonucleotide comprises a FRET acceptor fluorophore and the second forward oligonucleotide or the second reverse oligonucleotide comprises a FRET donor fluorophore.

31. The kit of claim 18, wherein the first forward oligonucleotide or the first reverse oligonucleotide comprises a quenched dye or detectable group and the second forward oligonucleotide or the second reverse oligonucleotide comprises a quenching moiety.

32. The kit of claim 18, wherein the first forward oligonucleotide or the first reverse oligonucleotide comprises a quenching moiety and the second forward oligonucleotide or the second reverse oligonucleotide comprises a quenched dye or detectable group.

33. The kit of claim 18, further comprising a double-stranded nucleic acid binding dye.

34. The kit of claim 18, wherein each of the first forward oligonucleotide, the second forward oligonucleotide, the first reverse oligonucleotide, or the second reverse oligonucleotide is from 5 to 35 nucleotides in length.

35. The kit of claim 18, further comprising a buffer.

36. The kit of claim 18, further comprising a salt.

37. The kit of claim 18, wherein the kit does not comprise an enzyme.

38. The kit of claim 18, wherein the kit does not comprise a nucleotide.

39. The composition of claim 3, wherein the alkyne is cycloctyne.

40. The kit of claim 24, wherein the alkyne is cycloctyne.

* * * * *